United States Patent
Wong et al.

(10) Patent No.: US 8,486,914 B2
(45) Date of Patent: Jul. 16, 2013

(54) HIRSUTELLA SINENSIS MYCELIA COMPOSITIONS AND METHODS FOR TREATING SEPSIS AND RELATED INFLAMMATORY RESPONSES

(75) Inventors: Chi-Huey Wong, La Jolla, CA (US); Alice L. Yu, La Jolla, CA (US); Wen-Bin Yang, Shenkeng Township (TW); Eugene Fan, La Jolla, CA (US); Hsien-Yeh Hsu, Taipei (TW); Peishan Lee, Taipei (TW); Tseng-Rong Tu, Taitung (TW); Chin-Chung Hung, Yuanlin (TW)

(73) Assignee: Academia Sinica, Taipei (TW)

( * ) Notice: Subject to any disclaimer, the term of this patent is extended or adjusted under 35 U.S.C. 154(b) by 316 days.

(21) Appl. No.: 12/750,655

(22) Filed: Mar. 30, 2010

(65) Prior Publication Data

US 2011/0028428 A1 Feb. 3, 2011

Related U.S. Application Data

(60) Provisional application No. 61/211,495, filed on Mar. 30, 2009.

(51) Int. Cl.
*A61K 31/715* (2006.01)

(52) U.S. Cl.
USPC ............................................................ 514/54

(58) Field of Classification Search
USPC ............................................................ 514/54
See application file for complete search history.

(56) References Cited

U.S. PATENT DOCUMENTS 5,441,943 A * 8/1995 McAnalley et al. ............ 514/54

OTHER PUBLICATIONS

The Merck Manual 16th Ed., 1999, pp. 339-342 and 1488-1490.*
Zhu et al, The Journal of Alternative and Complementary Medicine, 1998, 4(3), 289-303.*
Zhu et al, The Journal of Alternative and Complementary Medicine, 1998, 4(4), 429-457.*

* cited by examiner

*Primary Examiner* — Shaojia Anna Jiang
*Assistant Examiner* — Ganapathy Krishnan
(74) *Attorney, Agent, or Firm* — Eckman Basu LLP

(57) ABSTRACT

Compositions comprising *Hirsutella sinensis* mycelia extracts and chromatographically separated polysaccharide-enriched fractions thereof are provided. Methods for extracting *Hirsutella sinensis* mycelia are provided. Compositions for methods for their use in amelioration, prevention and treatment of sepsis, acute endotoxemia and inflammatory responses are disclosed.

5 Claims, 25 Drawing Sheets

Fraction WA3-1 DOSY Spectrum

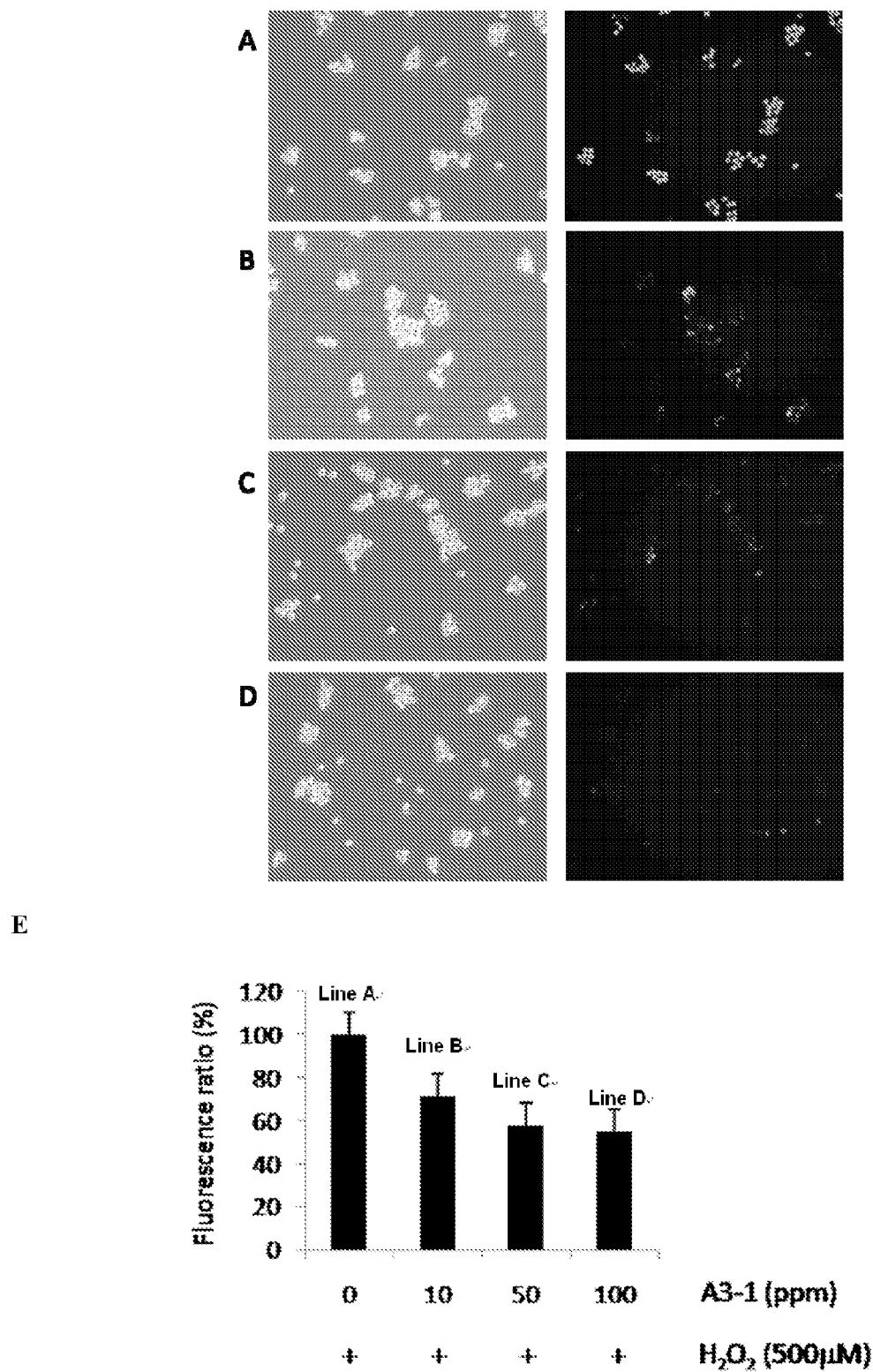
FIG. 14A – E

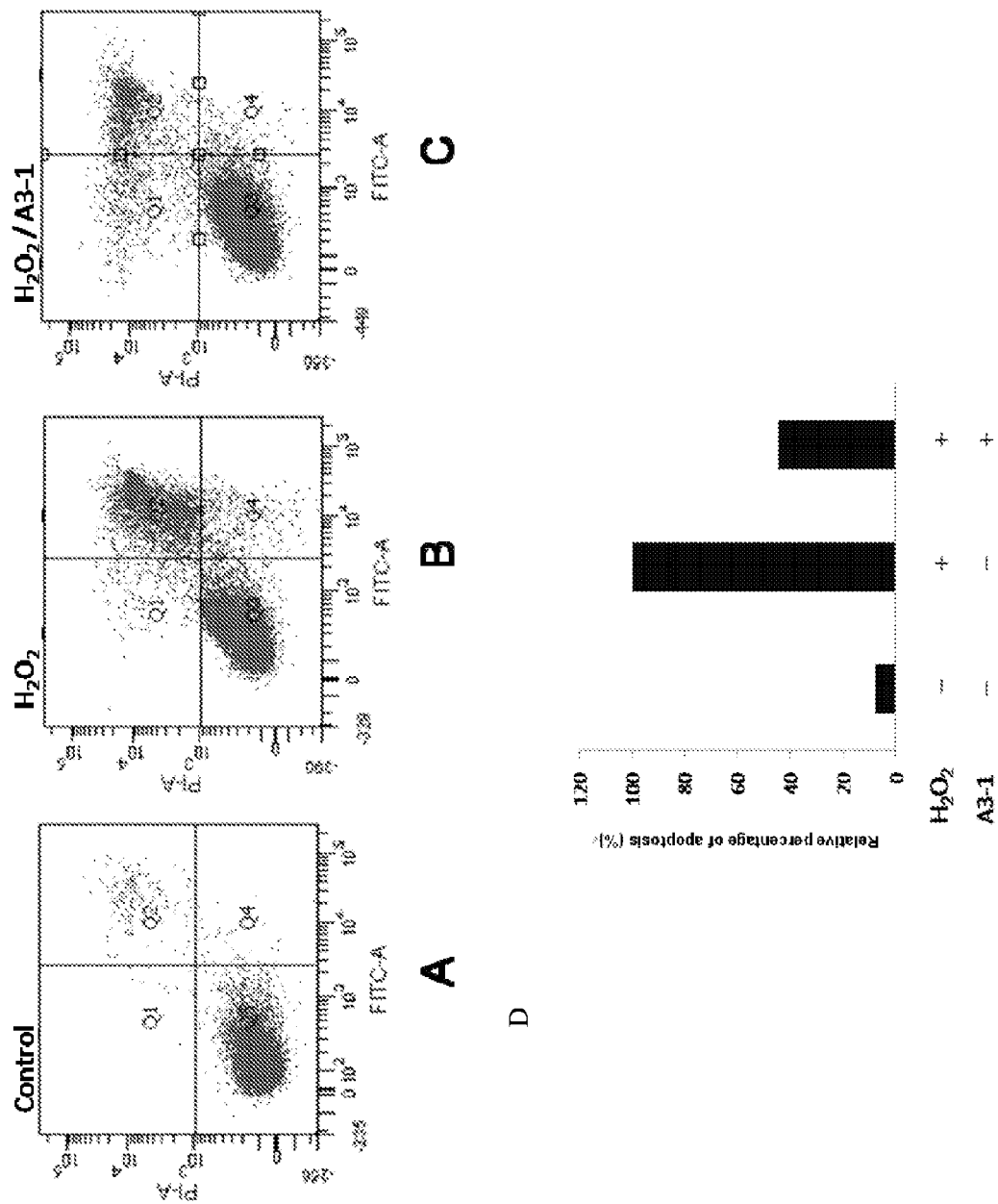
FIGS. 15A – D

HIRSUTELLA SINENSIS MYCELIA COMPOSITIONS AND METHODS FOR TREATING SEPSIS AND RELATED INFLAMMATORY RESPONSES

CROSS-REFERENCE TO RELATED APPLICATIONS

This application claims priority of U.S. provisional patent application Ser. No. 61/211,495, titled "COMPOSITIONS AND METHODS OF PREVENTING AND TREATING ACUTE ENDOTOXEMIA, SEPSIS AND OTHER INFLAMMATORY RESPONSES BY *HIRSUTELLA SINENSIS* MYCELIA (*CORDYCEPS SINENSIS*) EXTRACTS AND FRACTIONS" filed Mar. 30, 2009, the contents of which are incorporated herein in their entirety by reference.

TECHNICAL FIELD OF THE INVENTION

The present disclosure relates to compositions and methods for preventing or treating inflammatory responses. Specifically the invention relates to anti-inflammatory compositions isolated from *Hirsutella sinensis* mycelia.

BACKGROUND OF THE INVENTION

Sepsis is a systemic inflammatory response syndrome (SIRS) caused by an overwhelming immune response of the patient to invading microorganisms. When these microorganisms are lysed they release endotoxins in the blood, a condition called endotoxemia, which can lead to sepsis. Endotoxin released from the cell membranes of gram-negative organisms and cell wall fragments of gram-positive organisms is pathogenic. (Heumann D, et al. Curr Opin Microbiol 1998; 1:49-55.) The typical symptom of sepsis is a kind of hyperinflammatory state of the immune/inflammatory systems represented by elevated levels of pro-inflammatory mediators with development of multi-organ dysfunction syndrome and multi-organ failure (MOF). The body may develop this inflammatory response to microbes in the blood, urine, lungs, skin, or other tissues. (Levy M M, et al. Crit Care Med. 2003 April; 31(4):1250-1256.)

The initial infection can lead to an overwhelming reaction of the innate immune system with activation of proinflammatory cascades and appearance of various mediators, such as TNF-α, IL-1β and IL-6, resulting in SIRS and progressive MOF. The inflammatory cascade is mediated by cytokines, which are macrophage-derived, immunoregulatory peptides that target end-organ receptors in response to injury or infection. Cytokines can be categorized as either proinflammatory or antiinflammatory. Tumor necrosis factor-α, interleukin (IL)-1, and IL-6 are the most active proinflammatory cytokines released. (Matot I, et al. Intensive Care Med 2001; 27(suppl):3-9). At some point in sepsis, anti-inflammatory factors, such as IL-10, IL-1 receptor antagonist (IL-1RA), are released, perhaps representing a compensatory, anti-inflammatory response. Too much proinflammatory mediator release may trigger an uncontrolled, inflammatory response, resulting in consumptive depletion of the clotting system, and excessive release of anti-inflammatory mediators may contribute to immunosuppression or anergy, which occurs in humans with sepsis.

There is a need for effective treatments for inflammatory diseases and symptoms, including but not limited to sepsis, arthritis, inflammatory bowel diseases, multiple sclerosis and inflammation due to transplantation or viral infections.

*Cordyceps sinensis* (Berk.) Sacc., also known as Chinese caterpillar fungus and "Dong Chong Xia Cao," is a black, blade-shaped fungus found primarily at high altitudes in the mountains of northwest and southwest China. The fungus is parasitic, growing on and deriving nutrients from the larvae of moths in the genera *Hepialus* and *Thitarodes*. *Cordyceps sinensis* spores infect *Hepialus* and *Thitarodes* caterpillars in late summer or early fall while the caterpillars are hibernating underground. The fungus then multiplies by yeast-like budding and grows in the form of threadlike hyphae, ultimately killing the host. During the following spring, the fruiting body (i.e., the sexual, teleomorphic form) of the fungus grows out of the caterpillar's head and emerges above ground. Recent molecular evidence has revealed that *Hirstuella sinensis* is the true anamorph of the asexual-phase species of *Cordyceps sinensis*. (Chen Y-Q. et al. Biochemical Systemics and Ecology. (2001) 29: 597-607.

*Cordyceps sinensis* has been reported to produce both immuno-stimulating and immunosuppressive effects. Thus, it appears that *Cordyceps sinensis* may be a bi-directional modulator of the immune system. For example, some studies reported that *Cordyceps sinensis* enhances the activities of macrophages and natural killer (NK) cells, while other studies reported that the fungus inhibits these activities under different circumstances. *Cordyceps sinensis* has been shown to suppress or enhance antibody production and the proliferation of T cells, thymocytes, and natural killer cells. *Cordyceps sinensis* has also been shown to suppress or enhance expression of IL1, IL2, IL6, IL10, CD4, CD5, CD8, CD25, tumor necrosis factor, interferons, etc. US Pat. App. Pub. No. 20030095982 discloses a pulmonary function-improving fraction from *Cordyceps sinensis*. US Pat. App. Pub. No. 20040001817 discloses anti-aging nutritional supplements comprising *Cordyceps sinensis*.

Polysaccharides extracted from *Cordyceps sinensis* have been shown to alter apoptotic homeostasis, and to improve respiratory, renal and cardiovascular functions (Buenz et al., 2005, J Ethnopharmacol 96, 19-29; Zhu et al., 1998, J Altern Complement Med 4, 289-303; Zhu et al., 1998, J Altern Complement Med 4, 429-57), as well as to increase whole body sensitivity to insulin (Balon et al., 2002, J. Alternative Complementary Med 8, 315-23). However, the polysaccharide compositions of the extracts vary when the polysaccharides are extracted from different sources, from different strains, and under different growing conditions.

SUMMARY OF THE INVENTION

The present disclosure, in its many exemplary implementations, provides new compositions and methods relating to pharmaceutical compositions containing *Hirsutella sinensis* mycelia extracts or fractions to prevent and treat inflammatory diseases, acute endotoxemia and sepsis. The methods and compositions address treatment of acute endotoxemia as well as treatment of diseases, disorders, symptoms, immune reactions and responses often characterized with inflammation. The methods and compositions also address treatment of sepsis as well as improvement of septic shock conditions.

The invention relates to a composition comprising: a polysaccharide-enriched fraction of an extract of *Hirsutella sinensis* mycelia; and optionally, a pharmaceutically acceptable carrier, wherein the composition comprises an effective amount of extract to alleviate an inflammatory response. In some embodiments, the polysaccharide-enriched fraction comprises at least 50% polysaccharides, and further wherein the polysaccharides comprise at least 50% mannitol.

In some aspects, the composition comprises a size exclusion chromatographic sub-fraction of the polysaccharide-enriched fraction, wherein the sub-fraction comprises at least 90% polysaccharides. In some embodiments, the sub-fraction comprises at least 95% polysaccharides. In some embodiments, the sub-fraction has a molecular weight of about 27.5 kDa.

In some aspects, the sub-fraction comprises primarily galactomannans. In some embodiments, the sub-fraction comprises at least 50% galactose. In some embodiments, the sub-fraction comprises at least 35% mannose. In some embodiments, the sub-fraction comprises at least about 30% mannose, at least about 50% galactose, and about 10% or less of each of glucose and glucosamine.

The invention relates to a composition which comprises a sufficient amount of the sub-fraction to alter the levels of one or more of the cytokines IFN-γ, IL-10, IL-6, or IL-1α in a mammalian cell.

In some aspects, the polysaccharide-enriched fraction is prepared by a method comprising: extracting dried mycelia of *H. sinensis* with water; and isolating a water-soluble polysaccharide-enriched fraction. In some embodiments, the polysaccharide-enriched fraction is prepared by a method comprising: extracting dried mycelia of *H. sinensis* with water; isolating a water-soluble polysaccharide-enriched fraction; precipitating the water-soluble polysaccharide-enriched fraction with an alcohol to obtain a crude polysaccharide; and fractionating the crude polysaccharide by size exclusion chromatography to obtain a sub-fraction comprising about 90% or more of polysaccharides.

In some embodiments, the compositions of the invention comprise a pharmaceutical formulation suitable for administration to a patient in need thereof, further comprising a pharmaceutically acceptable excipient. In some embodiments, the formulation is suitable for administration to different parts of the body by a method selected from intravenous, intradermal, subcutaneous, oral, inhalation, transdermal, topical, transmucosal, and rectal administration.

The disclosure relates to a method for inducing expression of a cytokine in a mammalian cell, the method comprising: administering an effective amount of a composition according to the disclosure, sufficient to induce expression of a cytokine selected from IL-10, IL-1Ra and IL-1β.

In some embodiments, the induction of the expression of the cytokine results in the amelioration of a symptom associated with sepsis, acute endotoxemia syndrome or an inflammatory disease in a patient. In some embodiments, the induction of the expression of the cytokine results in protection against apoptosis in a patient. In some embodiments, the induction of the expression of the cytokine results in reduction of sepsis mortality in a patient. In some embodiments, the reduction of sepsis mortality is dose-dependent.

The disclosure relates to a method for treating an inflammatory response in a patient, the method comprising: administering a therapeutically effective amount of a formulation comprising the composition according to claim 2 and optionally, comprising a pharmaceutically acceptable excipient, to a patient in need thereof. In some embodiments, the administering is by a method selected from intravenous, intradermal, subcutaneous, oral, inhalation, transdermal, topical, transmucosal, and rectal administration.

In some embodiments, the treatment is prophylactic or therapeutic.

One aspect of the disclosure provides a new treatment method comprising providing a pharmaceutical composition containing at least *Hirsutella sinensis* mycelia extract and administering a therapeutically effective amount of the composition to a patient in need thereof.

According to another aspect of the present disclosure, a method is disclosed for preventing and treating acute endotoxemia. The method comprises the steps of providing a pharmaceutical composition containing at least *Hirsutella sinensis* mycelia extract and administering a therapeutically effective amount of the composition to a patient in need thereof.

A method is disclosed for preventing and treating a septic shock symptom, The method comprises the steps of providing a pharmaceutical composition containing at least *Hirsutella sinensis* mycelia extract and administering a therapeutically effective amount of the composition to a patient in need thereof.

According to another exemplary implementation, a pharmaceutical composition for preventing and treating acute endotoxemia is disclosed. The pharmaceutical composition comprises at least a partial purified fraction (designated A3-1 throughout the disclosure) of *Hirsutella sinensis* mycelia extract.

A pharmaceutical composition for preventing and treating a septic shock symptom is disclosed. The pharmaceutical composition comprises at least a partial purified fraction (A3-1) of *Hirsutella sinensis* mycelia extract.

In some instances a method is provided for preventing and treating an acute endotoxemia. The method comprises the steps of providing a pharmaceutical composition containing at least *Hirsutella sinensis* mycelia extract and administering a therapeutically effective amount of the composition to a patient in need thereof.

A method is disclosed for preventing and treating a sepsis disease. The method comprises the steps of providing a pharmaceutical composition containing at least *Hirsutella sinensis* mycelia extract and administering a therapeutically effective amount of the composition to a patient in need thereof.

In one aspect of the present disclosure, a method is provided for preventing and treating an acute endotoxemia. The method comprises the steps of providing a pharmaceutical composition containing at least a partial purified fraction (A3-1) of *Hirsutella sinensis* mycelia a extract and administering a therapeutically effective amount of the composition to a patient in need thereof.

A method is provided for preventing and treating a sepsis disease. The method comprises at least the steps of providing a pharmaceutical composition containing at least a partially purified fraction (A3-1) of *Hirsutella sinensis* mycelia extract and administering a therapeutically effective amount of the composition to a patient in need thereof.

In another aspect of the present disclosure, a method is provided for alleviating symptoms of sepsis. The method comprises at least the steps of providing it pharmaceutical composition containing at least *Hirsutella sinensis* mycelia extract or a partial purified fraction (A3-1) of *Hirsutella sinensis* mycelia extract; and administering an amount of the composition effective to increase at least one of an IL-10 and/or IL-1Ra level, whereby the symptoms of the acute endotoxemia are ameliorated.

A method is provided for alleviating symptoms of an auto-immune disease. The method comprises at least the steps of providing a pharmaceutical composition containing at least *Hirsutella sinensis* mycelia extract or a partially purified fraction (A3-1) of *Hirsutella sinensis* mycelia extract; and administering an amount of the composition effective to ameliorate the symptoms of an auto-immune disease. Such auto-immune diseases include, but are not limited to, systemic lupus erythematosus (SLE) a chronic, inflammatory autoimmune disorder, acute disseminated encephalomyelitis (ADEM), ankylosing spondylitis (AS), celiac diseases, Crohn's disease, Guillain-Barré syndrome (GBS), Hashimoto's disease, optic neuritis, Ord's thyroiditis, rheumatoid arthritis and temporal arteritis.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 13A shows hydrogen peroxide induced RAW264.7 cell damage in dose dependent manner. FIG. 13B shows abatement of hydrogen peroxide-induced cytotoxicity by A3-I in RAW264.7 cells.

FIGS. 14A-14E show the attenuation effects of A3-1 in hydrogen peroxide-induced intracellular ROS in RAW264.7 cells; the statistical analysis of the attenuation effects.

FIGS. 15A-15D show apoptosis detection after hydrogen peroxide and A3-1 co-treatment; the statistical analysis of a cellular population in apoptosis.

DETAILED DESCRIPTION OF THE INVENTION

Figure 1:
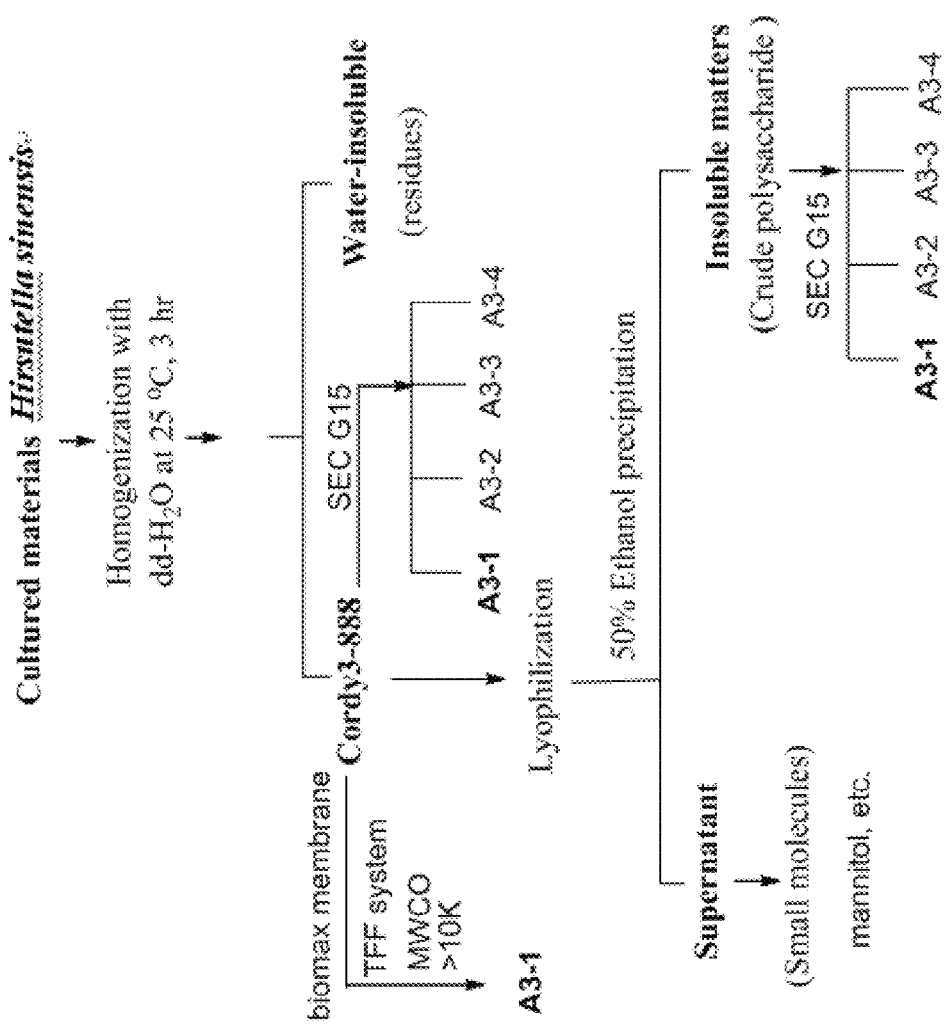
FIG. 1 shows an isolation flowchart of a *Hirsutella sinensis* mycelia water soluble extract (Cordy3-888) and Fraction A3-1 from *Hirsutalla sinensis*.

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, structural, functional, and other changes may be made without departing from the scope of the present disclosure. The following detailed description is, therefore, not to be taken in a limiting sense.

The term "*Hirsutella sinensis*" refers to the fungus named *Hirsutella sinensis*. It is an anamorph of *Cordyceps sinensis* (Berk.) Sacc. (*C. sinensis*), which is a well-known Chinese herbal medicine used in Asia. While other anamorphs for *Cordyceps sinensis* include *Cordyceps Synnematium sinensis, Paecilomyces hepialid*, etc. have been suggested only *Hirsutella sinensis* is a true anamorph. (Liu X J, et al. Acta Mycol Sin 1989, 8:35-40.)

The phrase "*Hirsutella sinensis* mycelia" refers to the fermentation product of *Hirsutella sinensis* fungus such as that manufactured by TCM Biotech International Corporation, Taiwan, with brand name TCM888, which also includes any tissue, part or fraction therefrom and/or any preparation thereof including homogenates, suspension, filtrates, filtration residues and solution.

The phrase "therapeutically effective amount" refers to an amount that produces some desired effect at a reasonable benefit/risk ratio applicable to any medical treatment. The effective amount may vary depending on such factors as the disease or condition being treated; the particular targeted constructs being administered, the size of the subject, or the severity of [he disease or condition. One of ordinary skill in the art may empirically determine the effective amount of a particular compound without necessitating undue experimentation.

The term "extract" refers to any solid, viscid, and liquid substance obtained through extraction from a given substance. In the present disclosure, a *Hirsutella sinensis* mycelia extract includes any solid, viscid, and liquid substance extracted from *Hirsutella sinensis* mycelia tissue.

*Hirsutella sinensis* is an anamorph of *Cordyceps*. *Cordyceps* is a precious resource in traditional Chinese medicine, Extracts of *Hirsutella sinensis* (*H. sinensis*) from cultured *Cordyceps* (*Hirsutella sinensis*) mycelia have a function against LPS induced septic shock in mice model and a purified polysaccharide A3-1 shows a similar effect. A rapid process to prepare *H. sinensis* polysaccharides is disclosed and identity of its sugar components determined.

Various methods and procedures for extraction are known and used by those skilled in the art, including the methods disclosed in U.S. Pat. No. 7,135,183, which is incorporated by reference herein in its entirety. Such methods and procedures include both physical and chemical processes, including solvent utilization, distillation, percolation, and supercritical fluid extraction. The extract may be further filtered or concentrated as desired. In one example, a *Hirsutella sinensis* mycelia extract is obtained by treating homogenized *Hirsutella sinensis* mycelia tissue with water for a predetermined time.

According to exemplary implementations of the present disclosure, the pharmaceutical composition may be in various forms including powders, creams, gels, salves, ointments, solutions, tablets, capsules, sprays, 3ud patches. Vehicles and carriers may be used for delivery of the composition to the patient. Such carriers include solubilizing agents, diluents, and dispersion media. These carriers are biocompatible, pharmaceutically acceptable, and do not alter the treatment characteristics of the extract. Excipients, adjuvants and other ingredients may also be included in the composition. The pharmaceutical composition may also be incorporated in cosmetics and skin care products that are applied topically.

The composition should be stable during manufacture and storage. The *Hirsutella sinensis* mycelia extract or specific constituents of the extract may be encapsulated, with agents such as aluminum monostearate, gelatin, and biodegradable and biocompatible polymers, to prevent undesired degradation in the body or by other ingredients in the composition. Anti-bacteria and anti-fungal agents such as butyl alcohols, parabens, chlorobutanol, phenol, ascorbic acid, and thimerosal may also be included in the composition.

The *Hirsutella sinensis* mycelia extract may induce IL-10 and/or IL-1Ra expression. In exemplary implementations, the increased expression of IL-10 and IL-1Ra plays a role in the abatement of allergies, allergic reactions, and symptoms of allergies. Inflammatory responses may be alleviated with increased IL-10 and/or IL-1Ra expression.

Other diseases and inflammatory symptoms associated with decreased IL-10 and/or IL-1Ra expression may also be treated with the composition containing *Hirsutella sinensis* mycelia extract. Examples include but are not limited to arthritis, inflammatory bowel diseases, multiple sclerosis, psoriasis and inflammation due to transplantation or viral infections.

Other diseases, disorders, and inflammatory symptoms associated with increased IL-1β and IL-6 levels may also be treated with the composition containing *Hirsutella sinensis* mycelia extract. Examples include but are not limited to endotoxemia and sepsis.

Administration of the composition may be achieved through various methods to different parts of the body, including intravenous, intradermal, subcutaneous, oral, inhalation, transdermal (i.e., topical), transmucosal, and rectal administration.

In other exemplary implementations, the composition is a solution or suspension injected parenterally, intradermally, or subcutaneously, Carriers include water, saline solutions, and other synthetic solvents. Buffers such as acetates, citrates, and phosphates may be used, as well as agents for adjusting tonicity, such as sodium chloride and dextrose, and agents for adjusting pH, such as hydrochloric acid and sodium hydroxide, All solutions are subject to sterile filtration through 0.22 micron membrane before use.

Material and Separation Procedures

Figure 2:
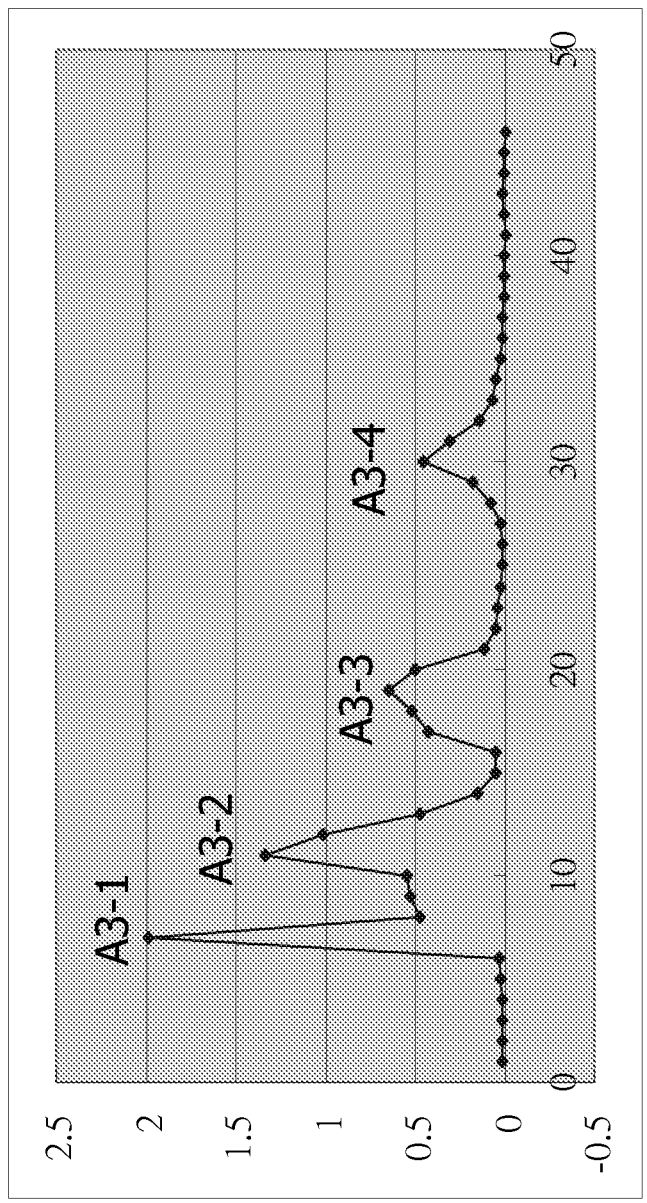
FIG. 2 shows the results of crude polysaccharide purification by SEC G-15 chromatography.

The dried myceliumof *H. sinensis* with brand name TCM888 were obtained from TCM Biotech International Corporation, Taiwan. The isolation flowchart was as shown in FIG. 1. Materials of *H. sinensis* 200 g was extracted three times with dd-water (200 mL×3) at room temperature (25° C.), each time for 3 h. Then the extract was combined and concentrated to give the 71 g (35%) crude water soluble extracts called Cordy3-888 and a water insoluble residue (129 g, 65%). The Cordy3-888 (10 g) was precipitated by adding 50 mL ethyl alcohol (50% EtOH in total volume 100 mL) to give supernatant and crude polysaccharide (2.5 g, 25%). The crude polysaccharide was further purified by size exclusion chromatography (with Sephadex® G-15) to give four sub-fractions called A3-1, A3-2, A3-3, and A3-4 with yields of 28%, 39%, 24%, 8%, respectively, as shown in FIG. 2. The four fractions were monitored and collected by phenol-sulfuric acid analysis.

Figure 3:
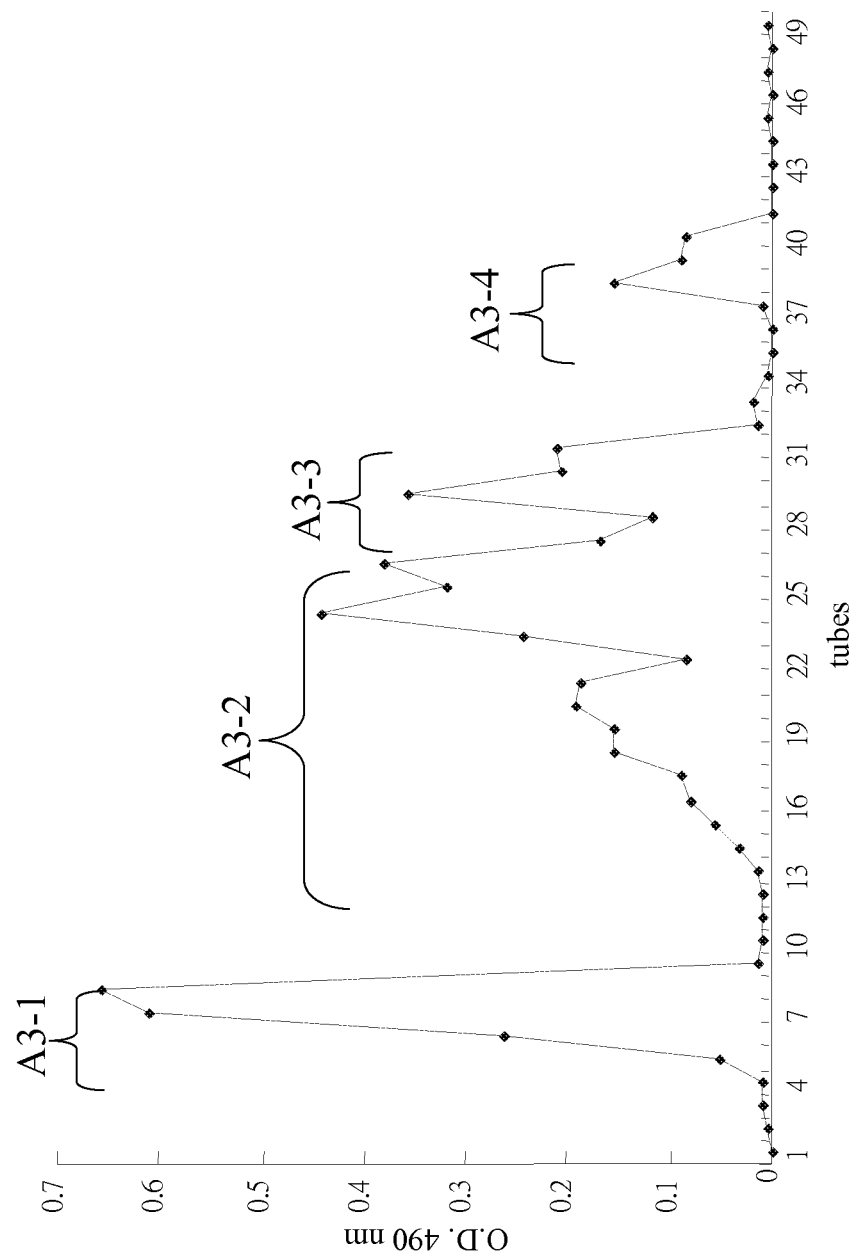
FIG. 3 shows the results of Cordy3-888 purification by SEC G-15 chromatography.

Without EtOH precipitation, 1 g of the Cordy3-888 was purified by size-exclusion chromatography (Sephadex® G-15) to give four sub-fractions also called A3-1, A3-2, A3-3, and A3-4 with yields of 12%, 49%, 27%, 10%, respectively, as shown in FIG. 3. Size exclusion chromatography (SEC) is a chromatographic method in which molecules in solution are separated based on their hydrodynamic volume. The four fractions were monitored and collected by the phenol-sulfuric acid analysis. For large scale preparation of A3-1, the Cordy3-888 109 was dissolved in 100 mL of dd-water and filtrated by Biomax® membrane (Millipore tangential flow filtration system, TFF) with molecular weight cut off (MWCO) 10 KDa to give A3-1 (9%). The molecular weights, sugar compositions and specific rotations of A3-1 fraction determined by both methods (SEC and TFF) are identical to one another.

NMR Analysis of Cordy3-888 and A3-1

Figure 4:
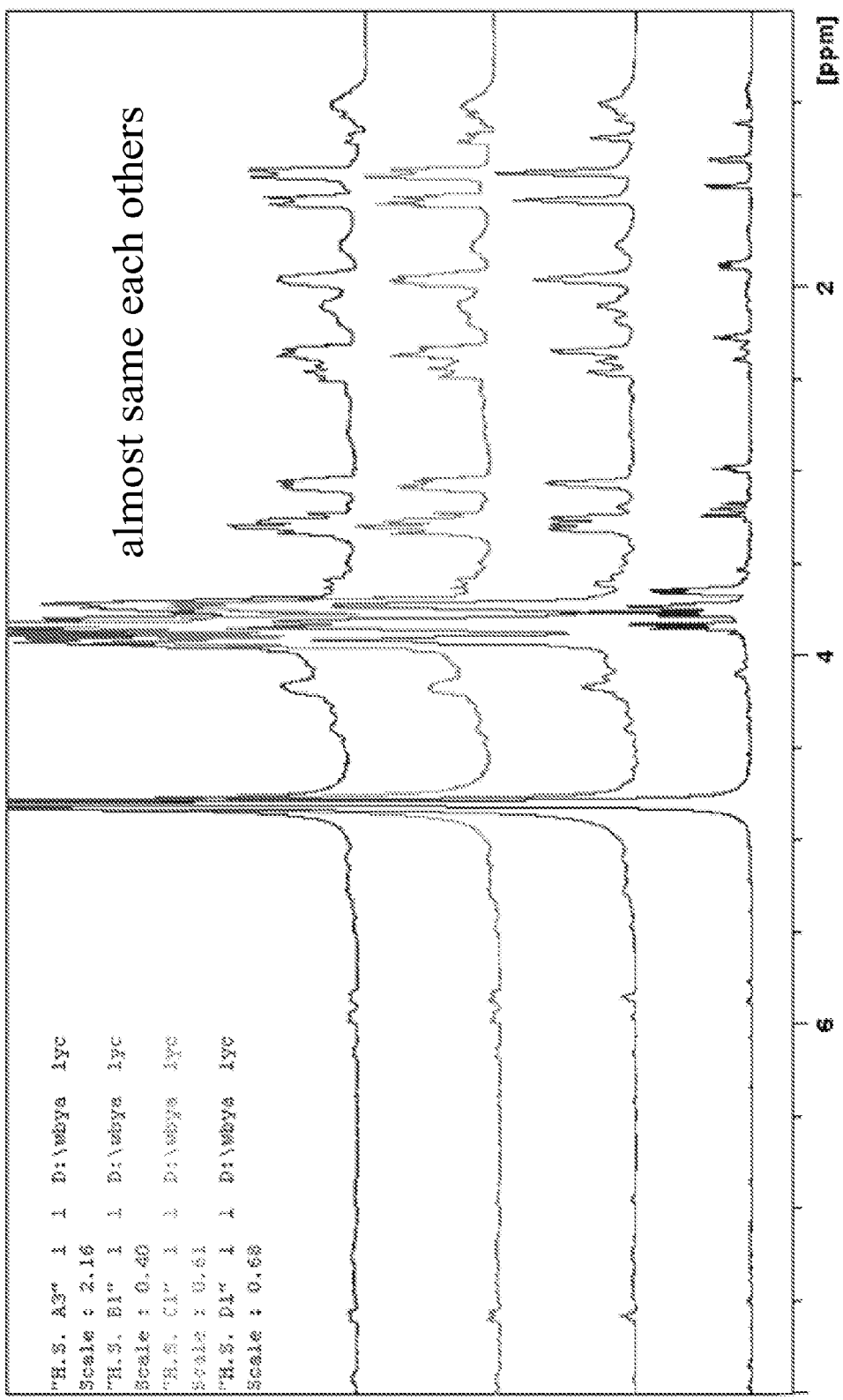
FIG. 4 shows $^1$H-NMR analysis of Cordy3-888 extracts from *H. sinensis*.

Cordy3-888 was obtained in various extraction procedures and these extracts following were analyzed by NMR spectrometry. The $^1$H-NMR results are shown in FIG. 4, procedure A3 (purple line): $H_2O$, 25° C., 3 hr, 42% yield; procedure B1 (green line): added trace amount $NaN_3$ in $H_2O$, 25° C., 24 hr, 38% yield; procedure C1 (red line): in $H_2O$, 25° C., 8 hr, 40% yield; procedure D1 (blue line): in $H_2O$, 100° C., 24 hr, 47% yield. All procedures showed an identifiable major component of mannitol and a minimal amount of saccharide in $^1$H-NMR spectrogram (FIG. 4).

Figure 5:
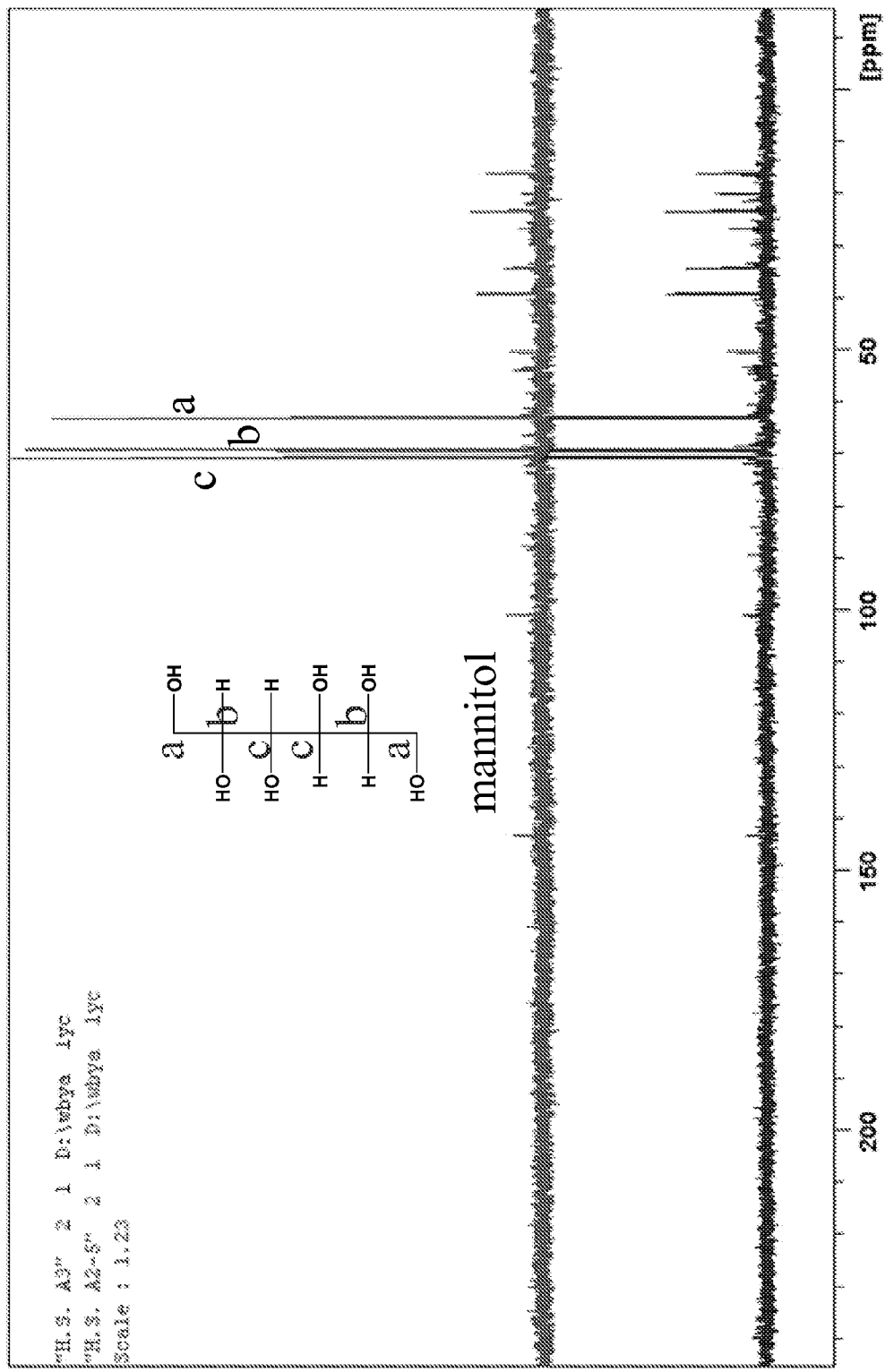
FIG. 5 shows $^{13}$C-NMR analysis of Cordy3-888 extracts from *H. sinensis*.

$^{13}$C-NMR also showed a consistent result in various extraction procedures with FIG. 5, where A2-5 (red line): $H_2O$, 25° C., 3 hr, 42% yield; A3 (blue line): $H_2O$, 25° C., 3 hr, 40% yield.

Figure 6:
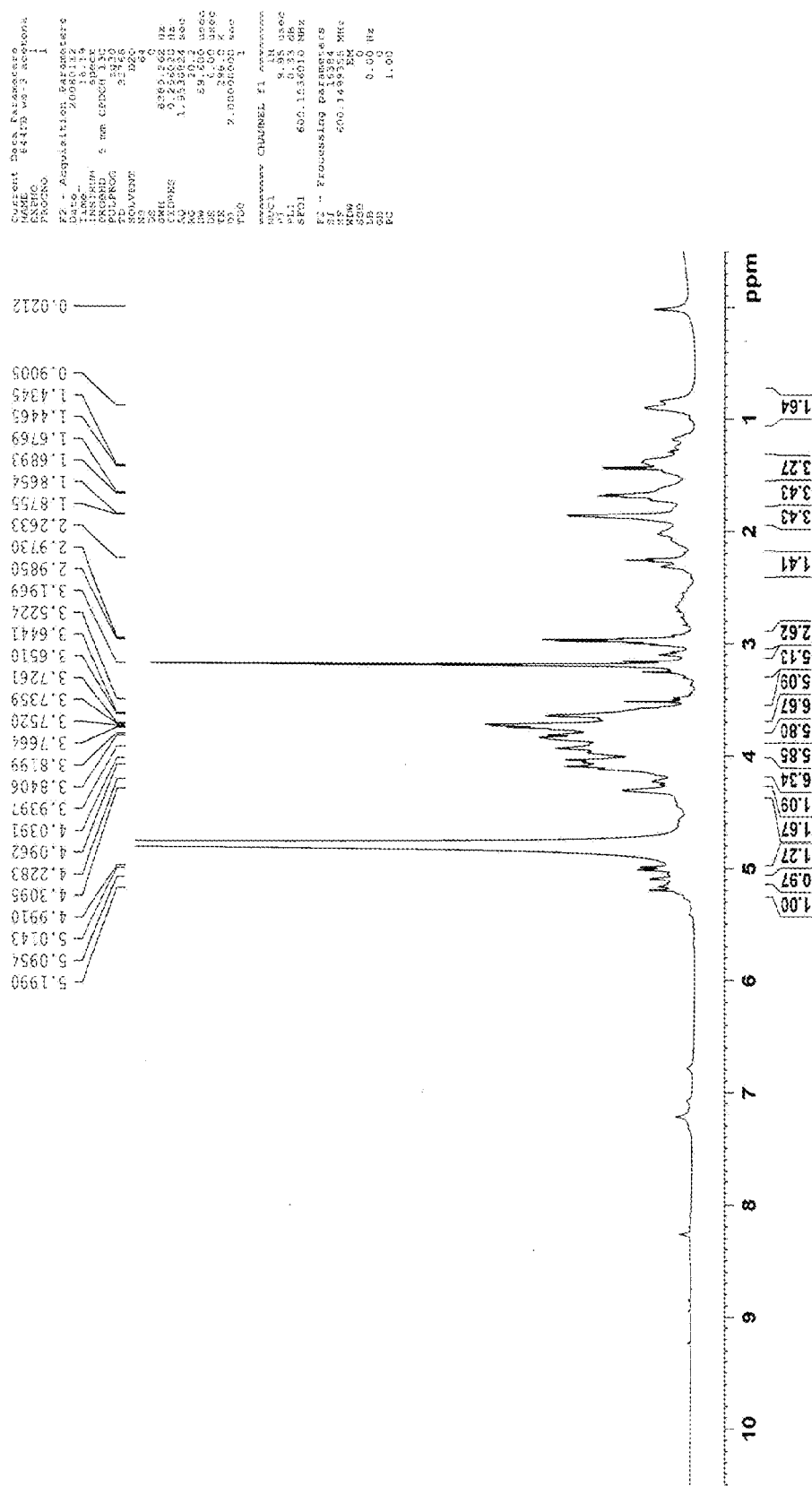
FIG. 6 shows $^1$H-NMR analysis of crude polysaccharide of *H. Sinensis*.

$^1$H-NMR analysis of crude polysaccharide from 50% EtOH precipitated Cordy3-888 is shown in FIG. 6. The spectrum showed a major composition of polysaccharide linked with some parts of peptides or lipids.

Figure 7:
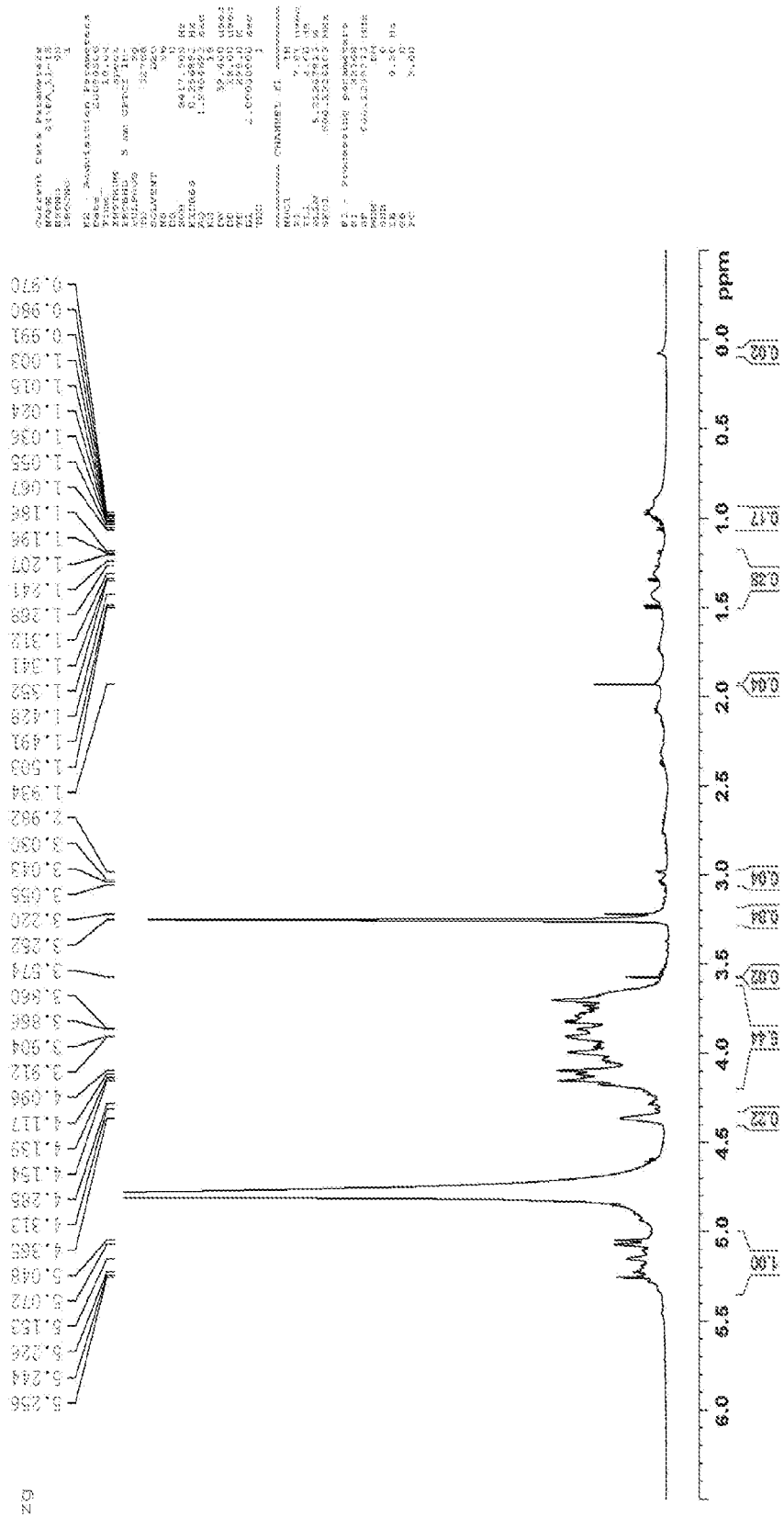
FIG. 7 shows $^1$H-NMR analysis of A3-1 by SEC G-15 chromatography from crude polysaccharide of *H. sinensis*.

FIG. 7 shows A3-1 spectrum which was isolated through SEC G-15 chromatography from crude polysaccharide of *H. sinensis*. The spectrum showed a high ratio of polysaccharide (>90%) in A3-1. Polysaccharide fraction A3-1 also can prepared from Cordy3-888 as a start material by SEC G-15 chromatography.

Figure 8:
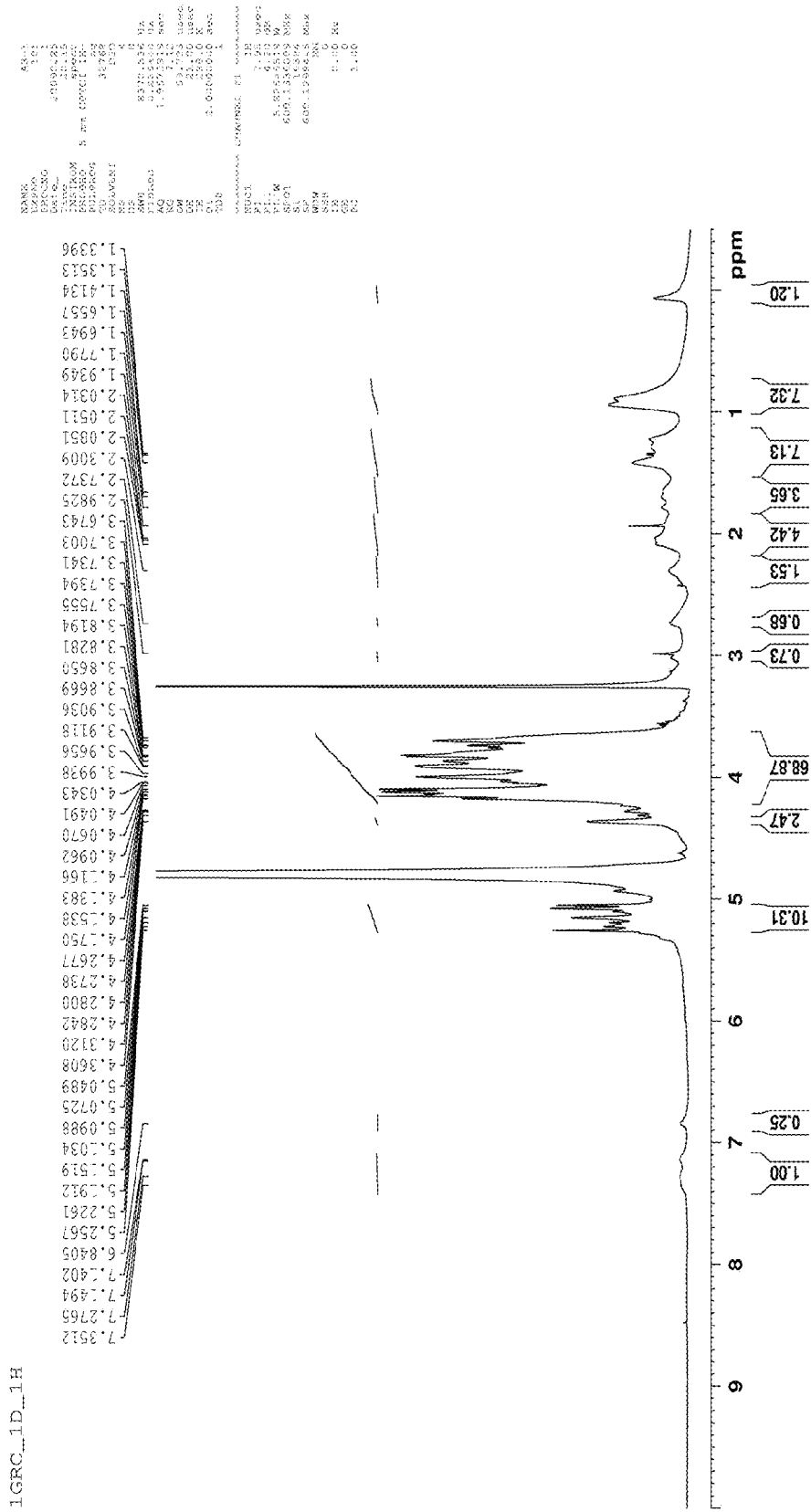
FIG. 8 shows $^1$H-NMR analysis of A3-1 by SEC G-15 chromatography from Cordy3-888.

As shown in FIG. 8, the $^1$H-NMR spectrum showed a high ratio of polysaccharide (>95%) in A3-1 fraction. And the $^1$H-NMR spectrum of A3-1 which was isolated by a Biomax® membrane (Millipore tangential flow filtration, TFF) system showed the identical peaks with other A3-1 fractions which were isolated from size exclusion chromatography.

Molecular Weight Analysis of Polysaccharide A3-1 by DOSY Experiment

Figure 9:
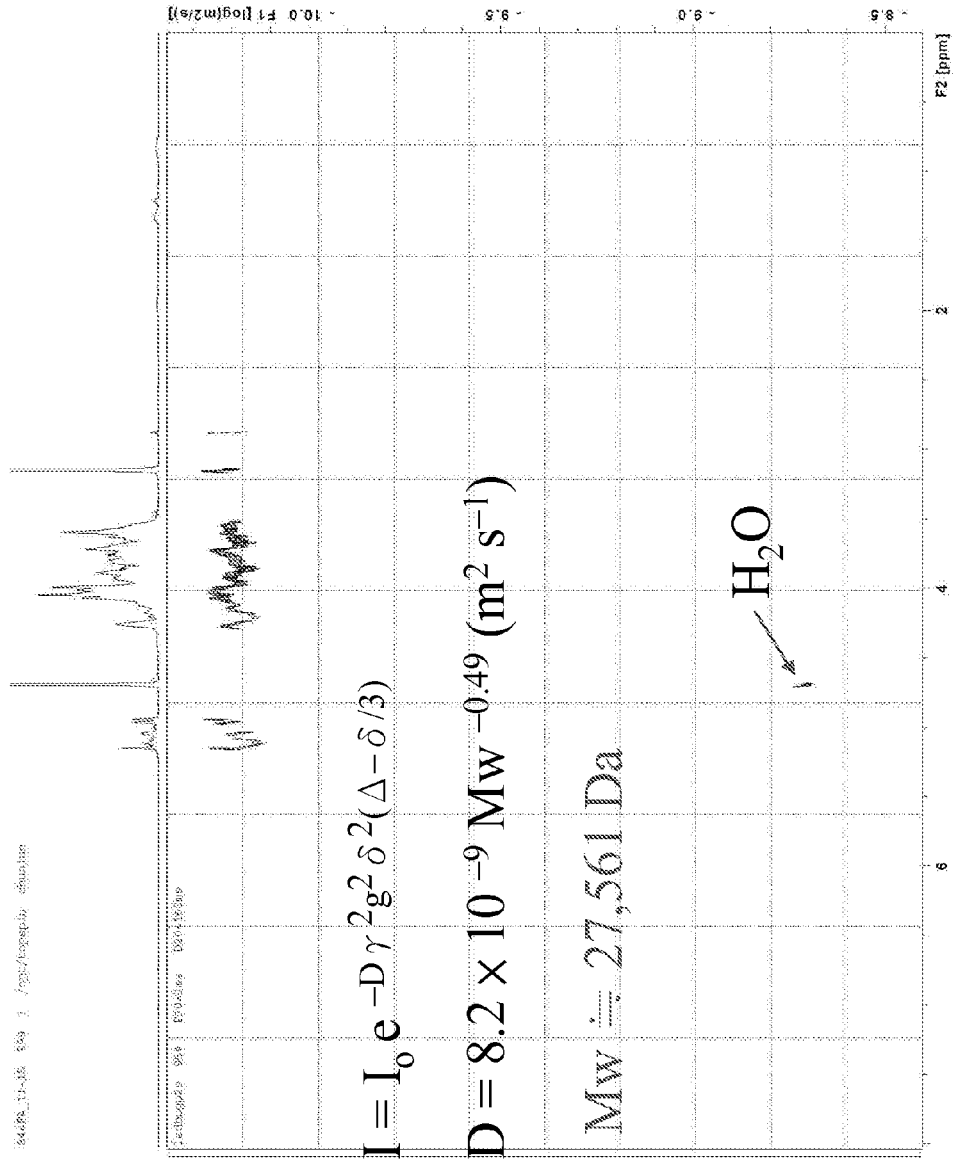
FIG. 9 shows the results of $^1$H-NMR DOSY experiment of A3-1 for molecular weight determination.

For molecular weight determination, polysaccharide fraction A3-1 was determined by diffusion-ordered spectroscopy (DOSY) experiment. This technique is used to deduce the estimated range of molecular weight. As the result the fraction A3-1 has a molecular weight of 27,561 Da, as shown in FIG. 9.

The water extract of *H. sinensis* was further fractionated by chromatography on size-exclusion Sephadex G-15 column. The bioactive polysaccharide fraction A3-1 was determined to have an average molecular weight of ~27 KDa, and its composition and structure were rigorously determined by a combination of chemical, enzymatic and spectroscopic methods. This is the first study that provides clear evidence for the structure-activity relationship of the polysaccharides in *H. sinensis*.

Figure 10:
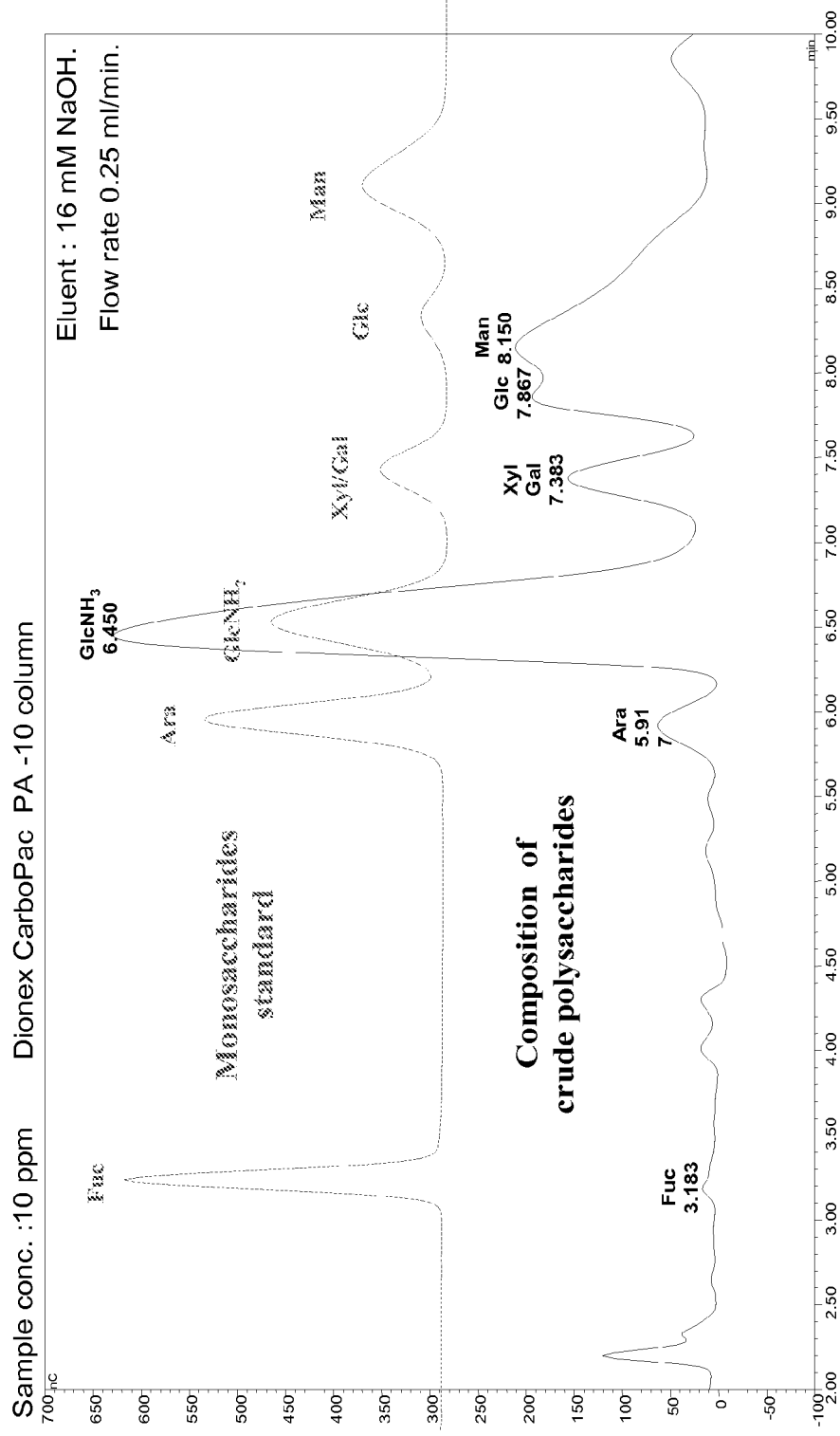
FIG. 10 shows the sugar composition of crude polysaccharide in HPAEC-PAD analysis.

Analysis of Monosaccharide Composition of Crude Polysaccharide, A3-1 and Other Fractions Each fraction (5 mg) was hydrolyzed with 4 M trifluoroacetic acid (TFA) at 112° C., in a sealed-tube for 12 hr. Excess acid was removed by co-distillation with water after the hydrolysis was completed. Each hydrolysate (1 mg) was dissolved in pure water (1 mg/mL). Twenty-five microliters of this solution was used for the ionic chromatography analysis by High Performance Anion Exchange Chromatography with Pulsed Amperometric Detection (HPAEC-PAD) analysis of Dionex® ICS-3000 System, eluted with a mixture of water and 200 mM NaOH in the volume ratio of 90:10. The sugar composition in HPAEC-PAD analysis showed that crude polysaccharide contains fucose 1%, arabinose 4%, glucosamine 52%, galactose 9%, glucose 9% and mannose 25%, respectively (Table 1 and FIG. 10).

TABLE I

Sugar composition of crude polysaccharide in HPAEC-PAD analysis.

| Sugar | Percentage (%) |
|---|---|
| Fucose | <1 |
| Arabinose | 4 |
| Glucosamine | 52 |
| Galactose/xylose | 9 |
| Glucose | 9 |
| Mannose | 25 |

TABLE 2

Sugar compositions of subfractions (A3-1 through A3-4) of Cordy3-888

| 20090308 | WA3-1 | WA3-2 | WA3-3 | WA3-4 |
|---|---|---|---|---|
| Crude polysaccharide (50% EtOH ppt) | | | | |
| Glc NH$_2$ | 2.79 | 20.83 | 5.74 | 12.32 |
| Gal | 56.44 | 7.46 | 25.58 | 22.11 |
| Glc | 1.70 | 11.21 | 10.07 | 10.68 |
| Man | 39.08 | 60.51 | 58.63 | 54.90 |
| Cordy 3-888 | | | | |
| Glc NH$_2$ | 0.74 | 41.90 | 56.41 | 49.88 |
| Gal | 58.33 | 24.51 | 8.21 | 12.55 |
| Glc | 3.13 | 28.42 | 34.13 | 33.94 |
| Man | 37.81 | 5.18 | 1.26 | 3.64 |

Figure 11:
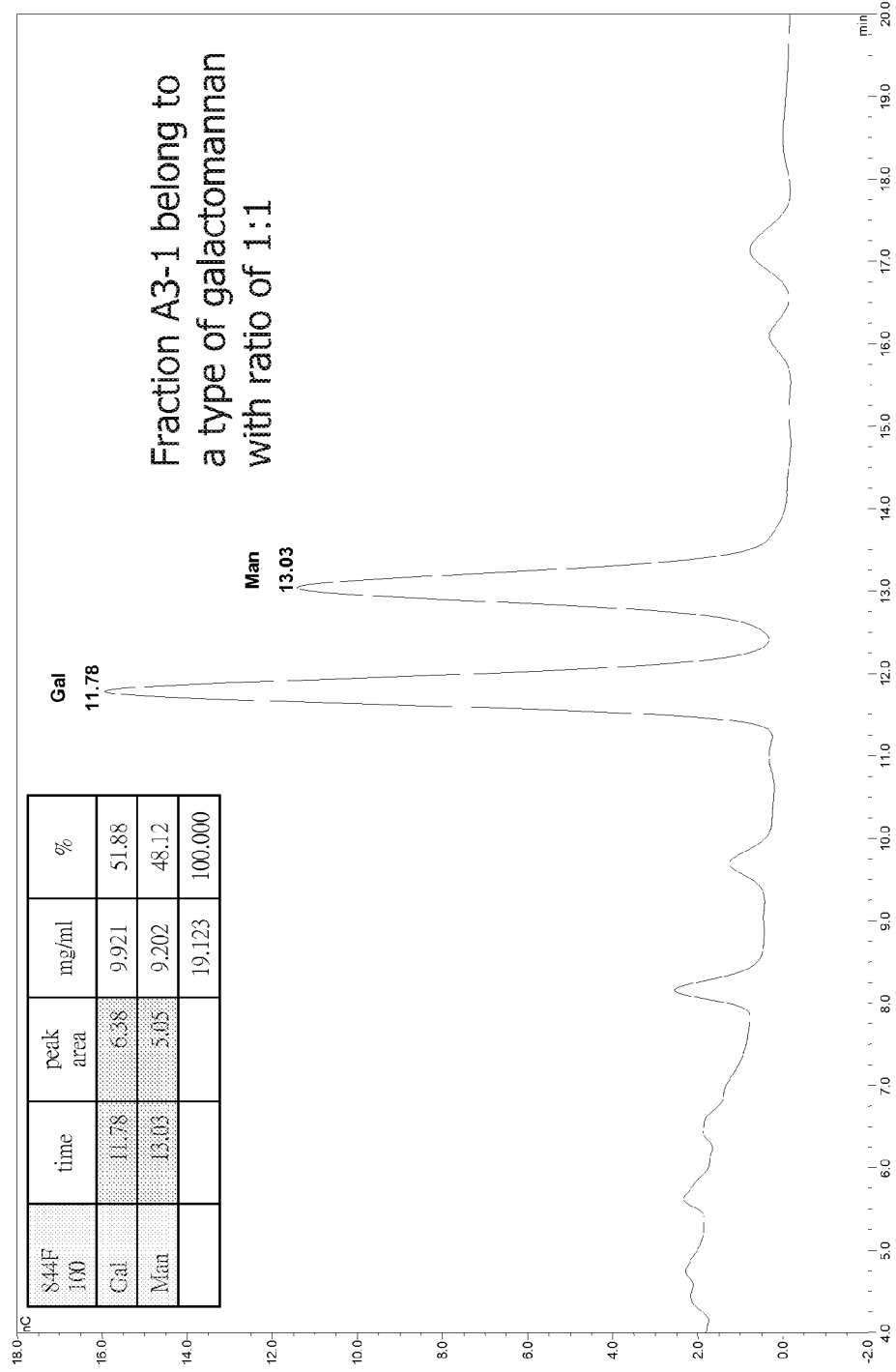
FIG. 11 shows the sugar composition of A3-I in HPAEC-PAD analysis.

The sugar compositions of both subfractions A3-1 and A3-4, which were isolated by size-exclusion chromatography (G-15) of Cordy3-888 and crude polysaccharide, are shown in Table 2 in HPAEC-PAD analysis. The A3-1 isolated from 50% EtOH precipitate of crude polysaccharide contains glucosamine 3%, galactose 56%, glucose 2% and mannose 39%, and the A3-1 isolated from Cordy3-888 by SEC chromatography contains glucosamine 1%, galactose 58%, glucose 3% and mannose 38%, respectively. (Table 2 and FIG. 11). Our study indicates that the polysaccharides in A3-1 of *H. sinensis* are mainly composed of monosaccharides Man and Gal. The glycosyl linkages of these monosaccharide residues were determined to give an insight into the structure of galactomannans. Our study showed that the linkages of galactomannan is α; β-(1→6); -(1→5)-D-Galf, and α; β-(1→4); -(1→6)-D-Manp and this fraction exhibited specific functions in murine splenocytes, including IFN-γ, IL-10, IL-6, and IL-1α. The results indicated that a high proportion of galactomannan exists in the A3-1 fraction.

Compositions

The compositions are standardized based on specific activities of defined properties which allows for very effective quality control based on standardized IC$_{50}$ based combinations. As discussed elsewhere in this application specific extraction procedures further facilitate the standardization of the compositions.

The compositions comprise *H. sinensis* preparations extracted with aqueous and/or organic solvents, which are then formulated to allow convenient (e.g., oral) drug delivery.

The compositions of the present invention can be in any form which is effective, including, but not limited to dry powders, grounds, emulsions, extracts, and other conventional compositions. To extract or concentrate the effective ingredients of the compositions, typically the *H. sinensis* part is contacted with a suitable solvent, such as water, alcohol, methanol, or any other solvents, or mixed solvents. The choice of the solvent can be made based on the properties of the active ingredient that is to be extracted or concentrated by the solvent. These ingredients can be extracted in the same step, e.g., using an alcoholic solvent, or they may be extracted individually, each time using a solvent which is especially effective for extracting the particular target ingredient. The content of active ingredient in the extract can be measured using HPLC, UV and other spectrometric methods.

The compositions of the present invention can be administered in any form by any effective route, including, e.g., oral, parenteral, enteral, intraperitoneal, topical, transdermal (e.g., using any standard patch), ophthalmic, nasally, local, non-oral, such as aerosal, inhalation, subcutaneous, intramuscular, buccal, sublingual, rectal, vaginal, intra-arterial, and intrathecal, etc. It can be administered alone, or in combination with any ingredient(s), active or inactive, including in a medicinal form, or as a food or beverage additive.

In preferred embodiments of the invention, the compositions are administered orally in any suitable form, including, e.g., extract, pill, capsule, granule, tablet or a suspension.

The compositions can be combined with any pharmaceutically acceptable carrier. By the phrase, "pharmaceutically acceptable carriers," it is meant any pharmaceutical carrier, such as the standard carriers described, e.g., Remington's Pharmaceutical Science, 21st Edition, Mack Publishing Company, 2005. Examples of suitable carriers are well known in the art and can include, but are not limited to, any of the standard pharmaceutical carriers such as a phosphate buffered saline solutions, phosphate buffered saline containing Polysorb 80, water, emulsions such as oil/water emulsion and various type of wetting agents. Other carriers may also include sterile solutions, tablets, coated tablets pharmaceutical and capsules. Typically such carriers contain excipients such as such as starch, milk, sugar, certain types of clay, gelatin, stearic acid or salts thereof, magnesium or calcium stearate, talc, vegetable fats or oils, gums, glycols. Such carriers can also include flavor and color additives or other ingredients. Compositions comprising such carriers are formulated by well known conventional methods. Generally excipients formulated with the compositions are suitable for oral administration and do not deleteriously react with it, or other active components.

Suitable pharmaceutically acceptable carriers include but are not limited to water, salt solutions, alcohols, gum arabic, vegetable oils, benzyl alcohols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose and the like. Other additives include, e.g., antioxidants and preservatives, coloring, flavoring and diluting agents, emulsifying and suspending agents, such as acacia, agar, alginic acid, sodium alginate, bentonite, carbomer, carrageenan, carboxymethylcellulose, cellulose, cholesterol, gelatin, hydroxyethyl cellulose, hydroxppropyl cellulose, hydroxypropyl methylcellulose, methylcellulose, octoxynol 9, oleyl alcohol, povidone, propylene glycol monostearate, sodium lauryl sulfate, sorbitan esters, stearyl alcohol, tragacanth, xanthan gum, and derivatives thereof, solvents, and miscellaneous ingredients such as microcrystalline cellulose, citric acid, dextrin, dextrose, liquid glucose, lactic acid, lactose, magnesium chloride, potassium metaphosphate, starch, and the like.

The compositions can also be formulated with other active ingredients, such as anti-oxidants, vitamins (A, C, ascorbic acid, B's, such as B1, thiamine, B6, pyridoxine, B complex, biotin, choline, nicotinic acid, folic acid, pantothenic acid, B12, cyanocobalamin, and/or B2, D, D2, D3, calciferol, E, such as tocopherol, riboflavin, K, K1, K2). Preferred compounds, include, e.g creatine monohydrate, pyruvate, L-Carnitine, α-lipoic acid, Phytin or Phytic acid, Co Enzyme Q10, NADH, NAD, D-ribose, amino acids such as L-glutamine, Lysine, chrysin; pre-hormones such as 4-androstenedione, 5-androstenedione, 4(or 5-)androstenediol, 19-nor-4 (or 5-)-androstenedione, 19-nor-4 (or 5-)-androstenediol, Beta-ecdysterone, and 5-Methyl-7-Methoxy Isoflavone.

Plants and botanicals can be formulated with the compositions of the present invention including, e.g., grape seed extract or other antioxidants, gingko or its extracts, *Panax ginseng, P. quinquefolium* or their extracts, Huangpi (*Clausena lansium*) or its extracts, Echinacea or its extracts, St John's Wort (*Hypericum perforatum*) or its extracts, Gegen (*Pueraria lobata*) or its extracts, Tianma (*Gastrodia elata*) or its extracts, *Armillariella mellea* or its extracts, Danshen (*Salvia miltiorrhiza*), or its extracts, Sanqi (*Panax notoginseng*) or its extracts, Monascus or Hongu (Red yeast rice), Huanqi (*Hedysarum polybotrys*) or its extracts, Dihuang (*Rehmannia glutinosa*) or its extracts, Danggui (*Angelica sinensis*), Yuanzhi (*Polygala tenuifoila*) or its extracts, Lingzhi (*Ganoderma* spp.) or its extracts, Fuling (*Poria cocos*) or its extracts, Gan Cao (*Glycyrrhiza uralensis* Fisch) or its extracts, Huperzine A, Lacithin, Metrifonate, Nocetile, and those mentioned in various text and publications or any combination thereof, e.g., E S Ayensu, Medicinal Plants of West Africa, Reference Publications, Algonac, Mich. (1978); L. Boulos, Medicinal Plants of North Africa, Reference Publications Inc., Algonac, Mich. (1983); and N. C. Shah, Botanical Folk Medicines in Northern India, J. Ethnopharm, 6:294-295 (1982).

Other active agents include, e.g., antioxidants, anti-carcinogens, anti-inflammatory agents, hormones and hormone antagonists, antibiotics (e.g., amoxicillin) and other bacterial agents, and other medically useful drugs such as those identified in, e.g., Remington's Pharmaceutical Sciences, 18th Edition, Mack Publishing Company, 1990. A preferred composition of the present invention comprises, optionally, a pharmaceutically-acceptable excipient.

The present invention relates to methods of administering the compositions, e.g., to prevent or ameliorate symptoms of sepsis, to treat sepsis or endotoxemia, to provide anti-apoptotic effects, to reduce sepsis mortality, to reduce inflammation, and other conditions and diseases as mentioned herein.

By the term "administering," it is meant that the compositions are delivered to the host in such a manner that it can achieve the desired purpose. The compositions can be administered to any host in need of treatment, e.g., vertebrates, such as mammals, including humans, male humans, female humans, primates, pets, such as cats and dogs, livestock, such as cows, horses, birds, chickens, etc.

An effective amount of the compositions are administered to such a host. Effective amounts are such amounts which are useful to achieve the desired effect, preferably a beneficial or therapeutic effect as described above. Such amount can be determined routinely, e.g., by performing a dose-response experiment in which varying doses are administered to cells, tissues, animal models (such as rats or mice in maze-testing, swimming tests, toxicity tests, memory tests as performed by standard psychological testing, etc.) to determine an effective amount in achieving an effect. Amounts are selected based on various factors, including the milieu to which the virus is administered (e.g., a patient with cancer, animal model, tissue culture cells, etc.), the site of the cells to be treated, the age, health, gender, and weight of a patient or animal to be treated, etc. Useful amounts include, 10 milligrams-100 grams, preferably, e.g., 100 milligrams-10 grams, 250 milligrams-2.5 grams, 1 gm, 2 gm, 3 gm, 500 milligrams-1.25 grams. etc., per dosage of different forms of the compositions prepared to contain the effective ingredients of the compositions, and injections, depending upon the need of the recipients and the method of preparation.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Cell Viability Assay

Figure 12:
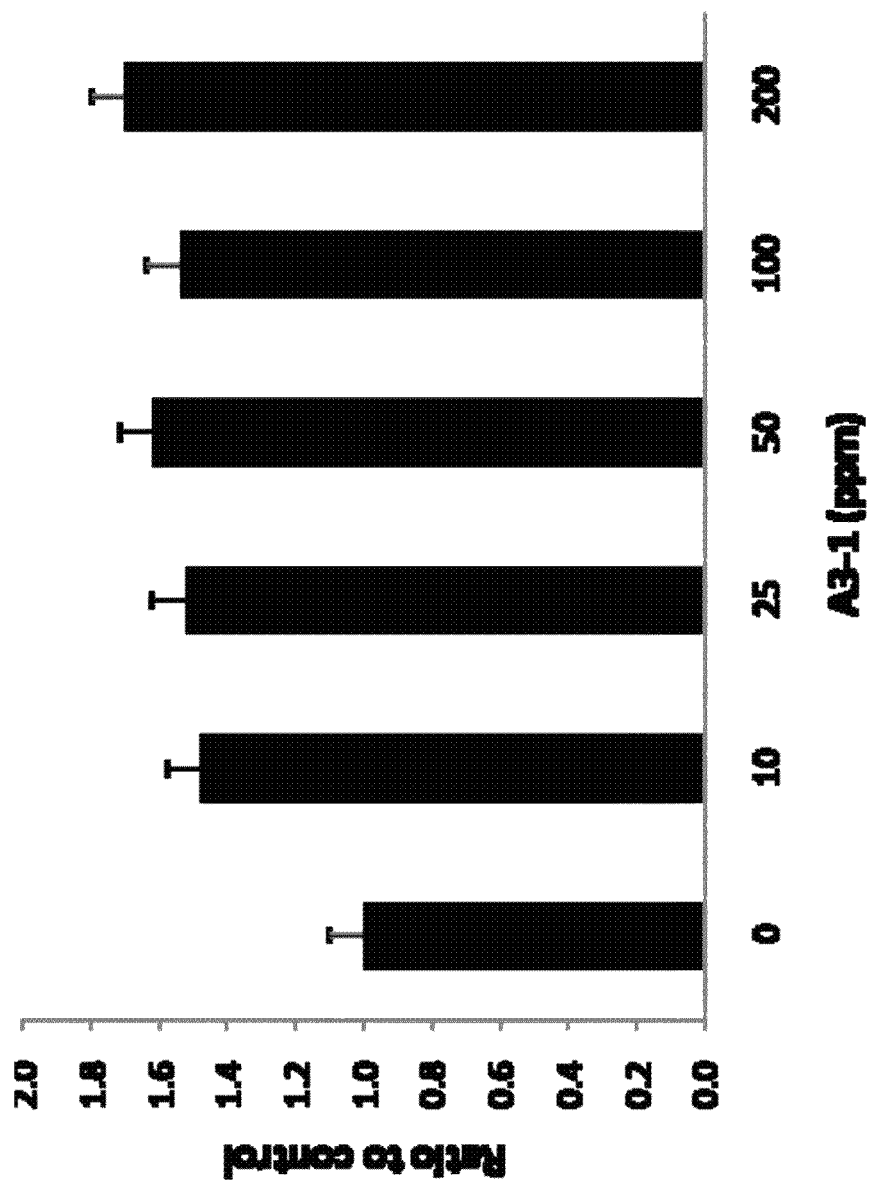
FIG. 12 shows the cytotoxicity of A3-1 on RAW264.7 cells measured in dose-dependent and the cell viability determined by the conventional MTT reduction assay.

Cell viability was assessed by the MTT (3-(4,S-dimethylthiazol-2-yl)-2,5-diphenyl tetrazolium bromide)) assay based on the reduction of MTT into formazan dye by active mitochondria. Briefly, the cells were placed in 96-well culture dishes at a density of $1\times10^5$ cells/ml in DMEM culture medium containing 10% PBS at 37° C., 5% $CO_2$. After attachment overnight, the cells were treated with different concentrations of A3-1 (0, 10, 25, 50, 100, 200 ppm) for 24 h (FIG. 12). Discarded supernatant, MTT solution (1 mg MTT/ml in PBS) was added to each well and incubated for 2 h. After washing, the formazan dye precipitates, the amount of which is proportional to the number of live cells, were dissolved in 100 µL of DMSO. The absorbance was read at 570 nm using a micro-plate reader (Thermo Varioskan Flash). Triplicate wells were analyzed at each concentration. This result shows fraction A3-1 has no cytotoxicity on RAW264.7 cells at doses of 10, 25, 50, 100, or 200 ppm.

Example 2

Figure 13A:
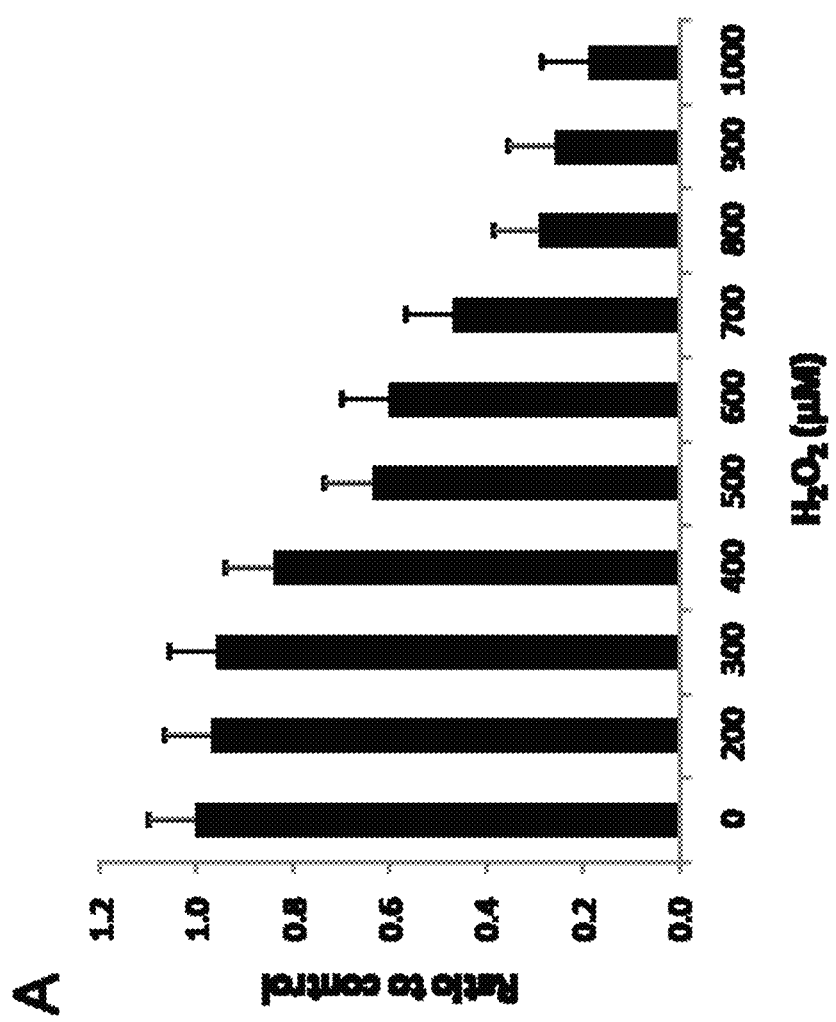
FIGS. 13A and 13B show protection effects of A3-1 in hydrogen peroxide mediated cell death in RAW264.7 cells.
Figure 13B:
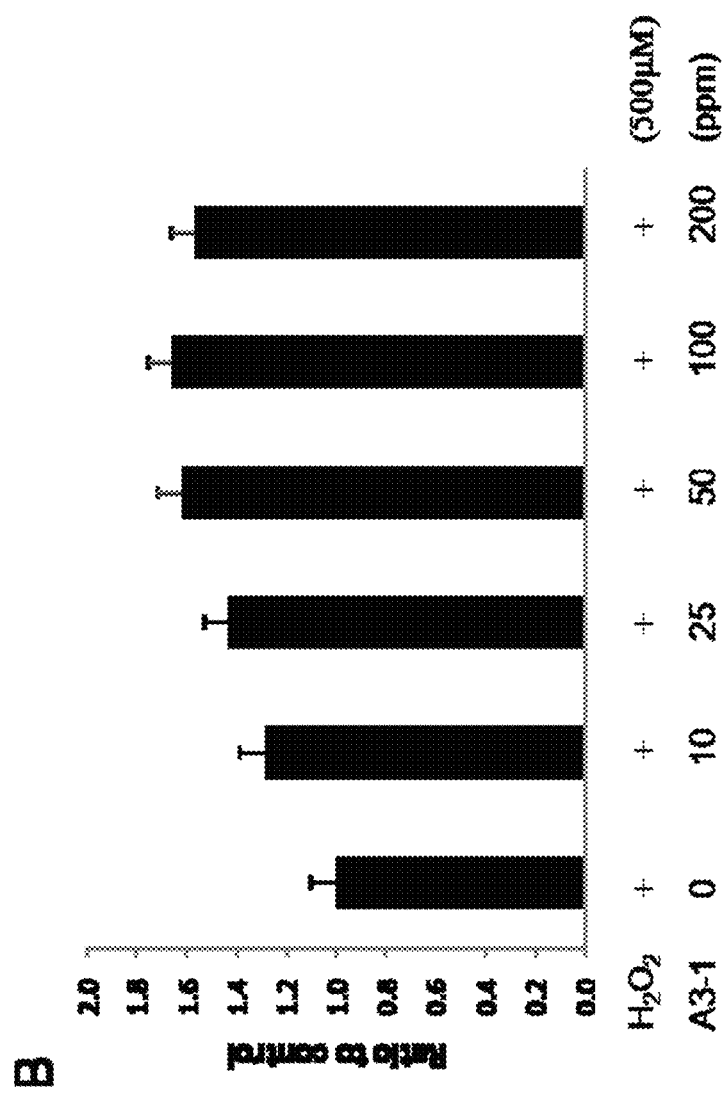

Protective Effects of A3-1 Against Hydrogen Peroxide-mediated Cell Death in RAW264.7 Cells The hydrogen peroxide-mediated RAW264.7 cells death is shown in FIG. 13A. The protective role of A3-1 which possesses strong antioxidant activity was tested in the hydrogen peroxide-mediated cell death assay (FIG. 13B). We also measured toxicity of A3-1 indicating that A3-1 is not harmful to RAW 264.7 cells in vitro (FIG. 12) until 200 ppm treatment. RAW264.7 cells were co-treated with hydrogen peroxide (500 µM) and A3.1 for 0, 10, 25, 50 and 100 ppm. The data are presented as mean±S.D. *P<0.05 compared to the group treated with hydrogen peroxide only (n=3), The viability of cells exposed to 500 MTT µM hydrogen peroxide for 24 h with A3-1 co-treatment had more than 60% better survival rate than without A3-1 co-treatment. The data showed that the hydrogen peroxide treatment seriously reduced the viability of cells, and A3-1 had exceptional protective effects on RAW264.7 cells from 50 to 100 ppm to against 500 µM of hydrogen peroxide induced cell death.

Example 3

Quenching $H_2O_2$-induced Intracellular ROS of A3-1 in RAW264.7 Cells

To investigate the mechanism by which A3-1 protects RAW264.7 cells during hydrogen peroxide injury, we analyzed intracellular reactive oxygen species (ROS) levels in RAW264.7 cells with fluorescent spectrometer. Cells were co-treated with 0, 10, 50, 100 ppm A3-1 and with 500 µM $H_2O_2$. Attenuation effects of AJ-1 in hydrogen peroxide-induced intracellular ROS in RAW264.7 cells. RAW264. 7 cells were treated with hydrogen peroxide (500 µM) and with 0, 10, 50, 100 ppm A3-1. After 30 min incubation, the cells were loaded with DCFH-DA for 10 min, washed, and measured by fluorescence spectroscopy. (FIG. 14A). Control with $H_2O_2$ only, (FIG. 14B). Co-treatment with $H_2O_2$ and 10 ppm A3-1, (FIG. 14C). Co-treatment with $H_2O_2$ and 50 ppm A3-1 (FIG. 14D). Co-treatment with $H_2O_2$ and 100 ppm A3-1. (FIG. 14E). The amount of intracellular ROS was quantified by microfluorometer with excitation and emission wavelengths at 490 nm and 530 nm, respectively. The results were confined in multiple experiments and presented as the mean±S.D., **p<0.01, n=3. After 24 h co-treatment, the fluorescence emission was analyzed by fluorescent spectrometer. After 30 min incubation, the cells were loaded with DCFH DA for 10 min, washed, and measured by fluorescence spectroscopy.

In FIG. 14, line A shows the control with $H_2O_2$ only, line B shows co-treatment with $H_2O_2$ and 10 ppm A3-1, line C shows co-treatment with $H_2O_2$ and 50 ppm A3-1, and line D shows co-treatment with $H_2O_2$ and 100 ppm A3-1. Hydrogen peroxide quenching experiment lead to the result that A3-1 at 100 ppm co-treatment with $H_2O_2$ shows the highest quenching ability for hydrogen peroxide induced ROS production in 24 h co-treatment (line D in FIG. 14E). FIG. 14 clearly illustrates A3-1 co-treatment with $H_2O_2$ shows a quenching ability for hydrogen peroxide induced ROS production in 24 h co-treatment in a concentration-dependent manner. More particularly, A3-1 at concentration of 100 ppm could destroy the ROS level significantly. When the concentration decreased to 10 ppm, the number of fluorescent cells also increased, which meant that the antioxidant activity of A3-1 acts in a concentration-dependent manner. In 24 h co-treatment, the fluorescence emission which was analyzed by fluorescent spectrometer yielded the same result. The amount of intracellular ROS was quantified by microfluorometer with excitation and emission wavelengths at 490 nm and 530 nm, respectively. The results were confirmed in multiple experiments and presented as the mean±SD, **p<0.01, n=3.

Example 4

The Rescue Effects of A3-1 on $H_2O_2$-induced Cell Apoptosis

Turning to FIG. 15, the ability of A3-1 to inhibit apoptosis induced by hydrogen peroxide on RAW264.7 cells was assessed through Annexin V-FITC and propidium iodine (PI) dual staining kit by flow cytometry. FIG. 15A shows control experiment (without $H_2O_2$ and A3-1). FIG. 15B shows the apoptosis was induced with 500 µM of hydrogen peroxide clearly appearing in Annexin V positive area (Q2 and Q4). FIG. 15C shows me ability of A3-1 to inhibit apoptosis induced with 500 µM of hydrogen peroxide at 100 ppm of A3-I. The horizontal (green fluorescence) and vertical (red fluorescence) axes represent labeling with Annexin V and PI, respectively. The lower left quadrant of the dot-plot graph represents viable non-apoptotic cells. Early apoptotic cells bind to annexin V in the Q4 area; late apoptotic cells bind to annexin V and take up PI in the Q2 area. The QI area contains cells that take up PI but do not bind to annexin V. These cells are most likely necrotic. This was shown as follows: FIG. 15D shows a statistical analysis of the cellular population in apoptosis. Left panel: exposures to without $H_2O_2$ and A3-1. Center panel: exposures to 500 µM $H_2O_2$, without A3-I. Right panel: exposures to 500 µM $H_2O_2$ and 100 ppm A3-1. Surprisingly, treatment with A3-I abolished apoptotic cells to less 50% than induced by hydrogen peroxide. Statistical analysis of cellular population in apoptosis was plotted against the apoptosis-inducing stimulus (FIG. 15). Only about 40% of cells undergo apoptosis in co-treatment 500 µM $H_2O_2$ and 100 ppm A3-1. These results suggest that A3-1 rescues programmed cell death apoptotic pathways induced by hydrogen peroxide. The percentage of apoptosis (Q2+Q4) is represented and the indicated data show means±SEMs of six samples in each group. *P<0.05 versus each other as indicated. #P<0.05 versus non-dialysate treated group.

Example 5

Validation of Bioactivity Via Fractionation of Crude Extracts of *H. sinensis*

Figure 16:
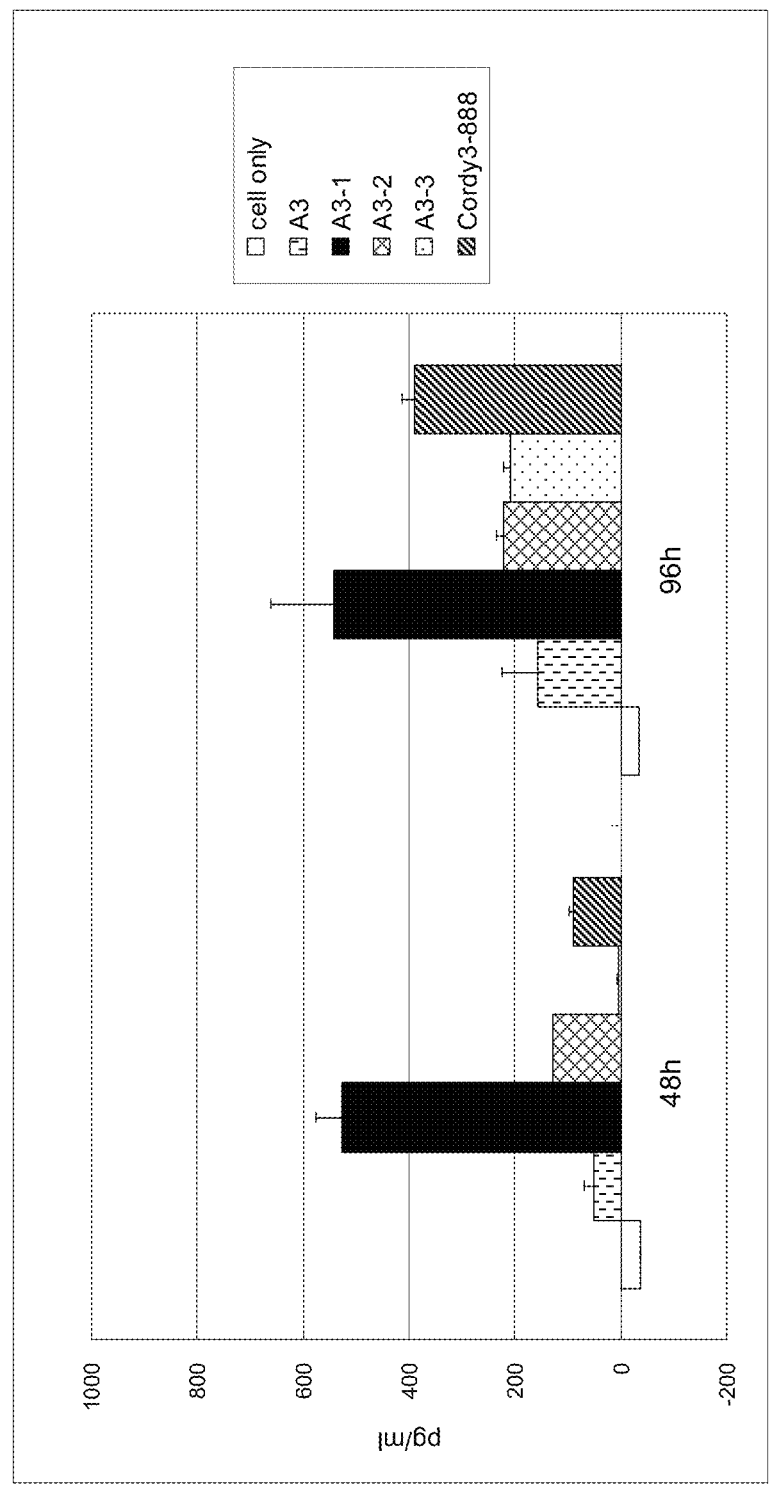
FIG. 16 shows IL-1β expression in various fractions measured by ELISA assay in mice splenocyte culture.

Previous studies revealed that galactomannan isolated from *H. sinensis* polysaccharides contained immuno-modulatory activities and antitumor activities. Here we found the fractions A3-1 and Cordy3-888 can induce the expression of IL-1β in mouse splenocytes model. Fresh spleen cells were harvested from BALB/c male mice (12 weeks old), suspended in RPMI Buffer Medium and their final concentration was adjusted to $1 \times 10^6$ cells/mL. Each *H sinensis* fraction 1 mg was added for this experiment. The IL-1β expressions of these polysaccharide fractions were measured by ELISA. FIG. 16 shows the IL1β expressions by treatments with various fractions: the blank with cell only (lane 1), fractions A3, A3-1, A3-2, A3-3 (lanes 2-5) and Cordy3-888 (lane 6). The A3-1 and Cordy3-888 exhibited good abilities to induce IL-IS expressions.

Example 6

Effect of *Hirsutella sinensis* Mycelia and A3-1 on IL-10 and IL1-Ra Cytokine Expression from Mice Spleen Cells Fresh spleen cells were harvested from BALB/c male mice (12 weeks old), suspended in RPMI-1640 medium containing 10% fetal calf serum and 100 μg/ml Penicillin/Streptomycin ("RPMI Buffer Medium"). The suspension was subjected to centrifugation to remove the supernatant. The cells collected were washed with PBS buffer twice-followed by treatment with KCL Lysis buffer (0.15N NH₄Cl, 1 mM NaHCO₃, 0.1 mM EDTA) for 10 min to destroy red blood cells. After KCL lysis buffer treatment, the cells were washed with PBS buffer again. The washed cells were resuspended in RPMI Buffer Medium and their final concentration was adjusted to $1 \times 10^6$ cells/mL in the same RPMI Buffer Medium. Sterile *Hirsutella sinensis* mycelia or A3-1 solution was prepared by dissolving *Hirsutella sinensis* mycelia or A3-1 in RPMI Buffer Medium both at a concentration of 200 ppm, followed by sterile filtration through 0.22 micron membrane before use. An equal volume of sterile *Hirsutella sinensis* mycelia or A3-1 solution and cell suspension was mixed to make *Hirsutella sinensis* mycelia final concentration at 100 ppm. For control without *Hirsutella sinensis* mycelia or A3-1, the *Hirsutella sinensis* mycelia or A3-1 solution was replaced with RPMI Buffer Medium. The cell suspensions with or without *Hirsutella sinensis* mycelia were incubated at 37° C. under 5% $CO_2$ for 24 hours. The culture supernatant was collected; IL-10 and IL-1Ra levels in supernatant were determined by enzyme-linked immunosorbent assay (ELISA) according to the manufacturer's instructions (R&D Systems, MN, U.S.A.). PBS represents Phosphate Buffered Saline.

TABLE 3

IL-10 and IL-1Ra expression of mouse splenocytes ($5 \times 10^5$ cells/mL) treated with *Hirsutella sinensis* mycelia (100 ppm) and A3-1 (100 ppm).

| | Expression of Cytokines | |
|---|---|---|
| Groups | IL-10 (pg/mL) | IL-1Ra (pg/mL) |
| Control, n = 3 | 20.5 ± 7.4 | 1863.2 ± 1001.4 |
| HSM (100 ppm), n = 3 | 117.8 ± 2.6 | 18992.8 ± 6458.4 |
| A3-1 | 168.4 ± 11.3 | 17720.7 ± 3455.7 |

The results from Table 3 above indicate *Hirsutella sinensis* mycelia and A3-1 can stimulate IL-10 and IL-1Ra cytokine expression from mice spleen cells.

Example 7

Effect of *Hirsutella sinensis* Mycelia Treatment on Serum Level of IL-10 and IL-1Ra Cytokines of BALB/c Mice Six-week-old male BALB/c mice were purchased from BioLASCO Taiwan Co., Ltd. Sterile *Hirsutella sinensis* mycelia solution for injection was prepared by dissolving *Hirsutella sinensis* mycelia ill phosphate buffer saline (PBS) at a concentration of 200 mg/mL, followed by sterile filtration through 0.22 micron membrane before use. Mice were intraperitoneally administrated. 0.2 ml *Hirsutella sinensis* mycelia solution (60 mg/Kg or 75 mg/Kg body weight) or 0.2 ml of Normal Saline (control), and bled from the submandibular vein 1.5 and 6 hours later. Cytokine IL-10 and IL-1Ra levels in the plasma were determined by enzyme-linked immunosorbent assay (ELISA) according to the manufacturer's instructions (R&D Systems, MN, USA).

TABLE 4

Effect of *Hirsutella sinensis* mycelia treatment on serum level of IL-10 and IL-1Ra cytokines of BALB/c mice

| Time after HSM treatment (hours) | Group | Cytokine Concentration in Plasma | |
|---|---|---|---|
| | | IL-10 (pg/ml) | IL-1Ra (pg/ml) |
| 1.5 | Control | 3.5 ± 2.1 | 10.4 ± 18.4 |
| | HSM 1.5 μg | 4.6 ± 4.6 | 38.9 ± 25.2 |
| | HSM 1.2 mg | 19.9 ± 9.7* | 366.2 ± 143.7* |
| 6 | Control | 3.8 ± 2.6 | 80.90 ± 45.4 |
| | HSM 1.5 μg | 6.6 ± 5.3 | 115.6 ± 79.5 |
| | HSM 1.2 mg | 9.8 ± 3.7 | 293.7 ± 63.4* |

Data represents mean ± SD (n = 6). *Hirsutella sinensis* mycelia pretreatment (HSM), *P < 0.05 compared to control mice.

The results in Table 4 indicate that within 1.5 and 6 hours after treatment by *Hirsutella sinensis* mycelia, BALB/c mice exhibit a significant increase in serum cytokine IL-10 and IL-1Ra level. Our current findings clearly demonstrate that *Hirsutella sinensis* mycelia alters the expression of the serum cytokine level, which may help to alleviate acute endotoxemia symptoms.

Example 8

Figure 17:
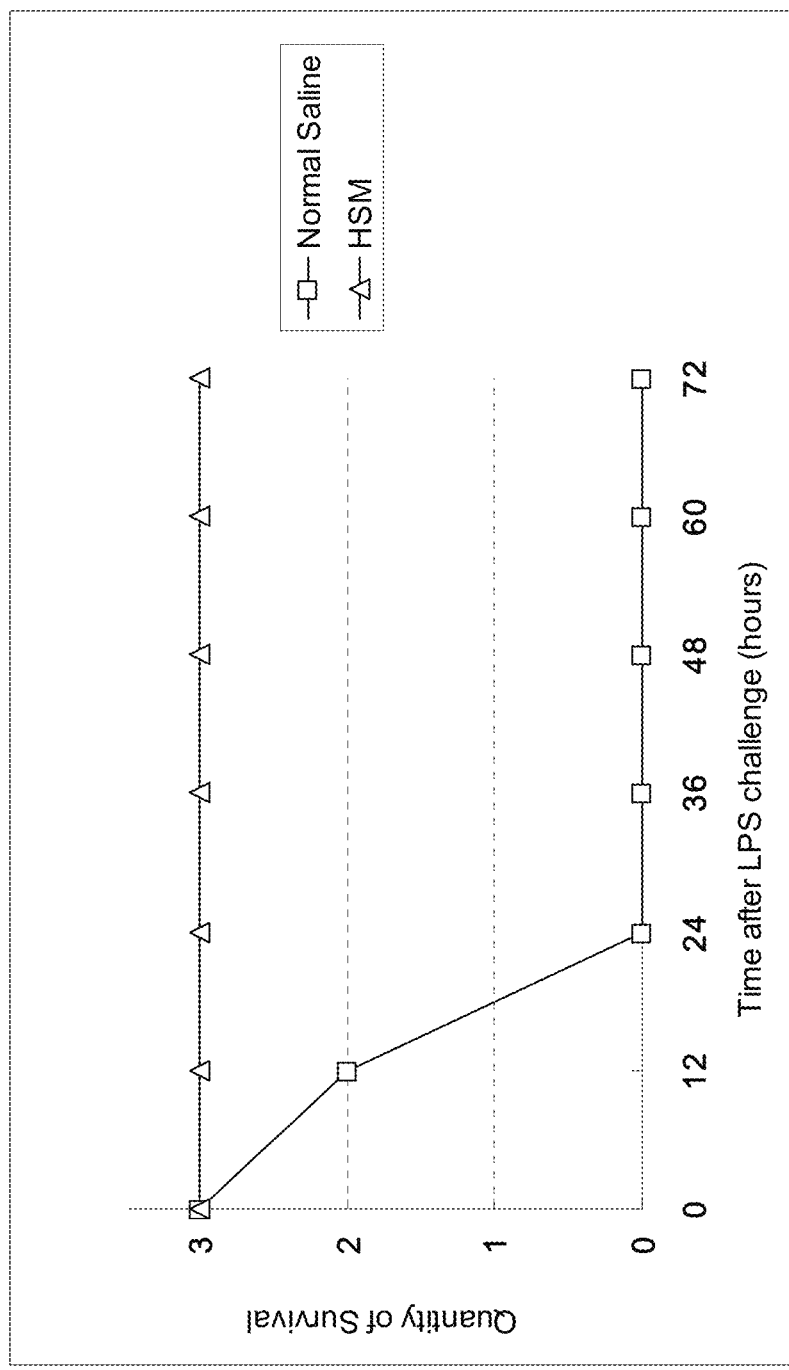
FIG. 17 demonstrates the efficacy of *Hirsutella sinensis* mycelia extract against LPS challenge.

Six-weeks-old BALB/c mice were pretreated with *Hirsutella sinensis* mycelia extract 48 hours before LPS challenge by intraperitoneal injection (i.p.) of 120 mg of *Hirsutella sinensis* mycelia extract dissolved in normal saline. On day 0, 6 mice were challenged with LPS (0.25 mg/20 g mouse; 12.5 mg/Kg) intraperitoneally. The mortality of mice was monitored in 12-hour intervals for 3 days. Data represent survival quantity (n=3). Study groups included Normal saline pretreatment (Control) and *Hirsutella sinensis* mycelia pretreatment (HSM). The results are shown in FIG. 17. The results from FIG. 17 indicate *Hirsutella sinensis* mycelia can ameliorate the symptoms of the acute endotoxemia syndrome and significantly reduce LPS-induced sepsis mortality.

Example 9

Figure 18:
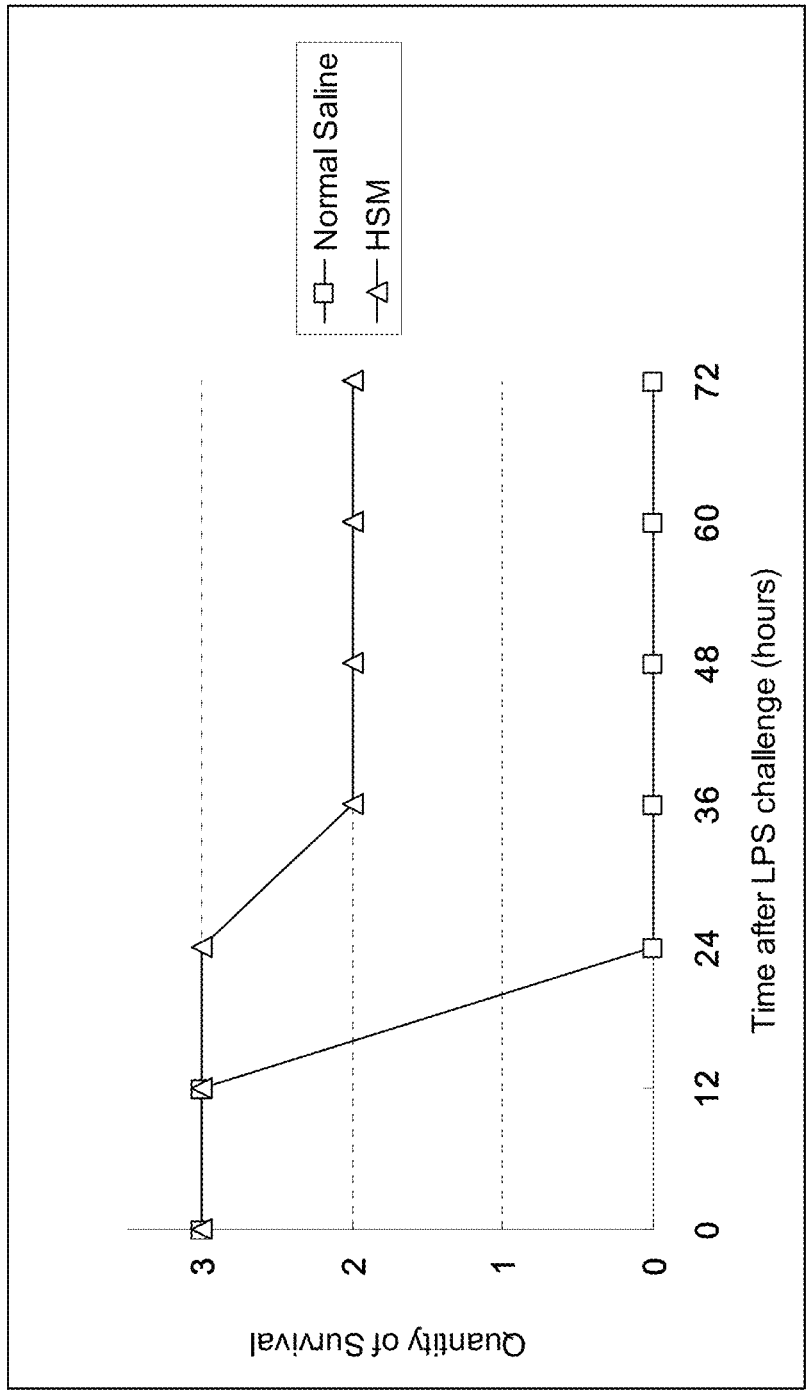
FIG. 18 shows the first re-examination of the efficacy of *Hirsutella sinensis* mycelia extract against LPS challenge.

Six-weeks-old BALB/c mice were pretreated with *Hirsutella sinensis* mycelia extract 48 hours before LPS challenge by i.p. of 120 mg of *Hirsutella sinensis* mycelia extract dissolved in normal saline. On day 0, 6 mice were challenged with LPS (0.25 mg/20 g mouse; 12.5 mg/Kg) intraperitoneally. The mortality of mice was monitored in 12-hour intervals for 3 days. Data represent survival quantity (n=3). Study groups included Normal saline pretreatment (Control) and *Hirsutella sinensis* mycelia pretreatment (HSM). The results are shown below (FIG. 18). The results from FIG. 18 indicate *Hirsutella sinensis* mycelia can ameliorate the symptoms of the acute endotoxemia syndrome and reduce LPS-induced sepsis mortality.

Example 10

Figure 19:
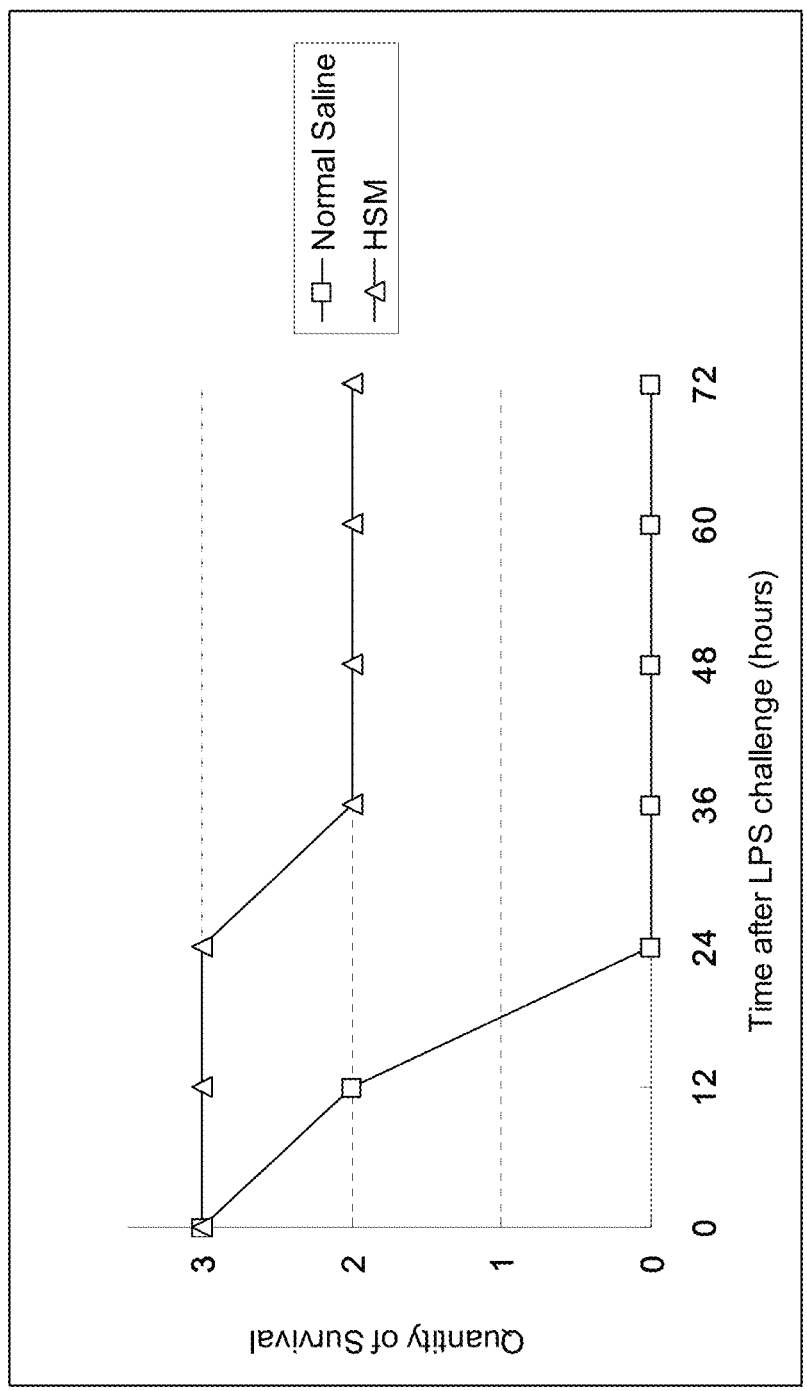
FIG. 19 shows the second re-examination of the efficacy of *Hirsutella sinensis* mycelia extract against LPS challenge.

Six-weeks-old BALB/c mice were pretreated with *Hirsutella sinensis* mycelia extract 48 hours before LPS challenge by i.p. of 120 mg of *Hirsutella sinensis* mycelia extract dissolved in normal saline. On day 0, 6 mice were challenged with LPS (0.25 mg/20 g mouse; 12.5 mg/Kg) intraperitonealy. The mortality of mice was monitored in 12-hour intervals for 3 days. Data represent survival quantity (n=3). Study groups included Normal saline pretreatment (Control) and *Hirsutella sinensis* mycelia pretreatment (HSM). The results are shown below (FIG. 19). The results from FIG. 19 above indicate *Hirsutella sinensis* mycelia can ameliorate the symptoms of the acute endotoxemia syndrome and reduce LPS-induced sepsis mortality.

Example 11

Figure 20:
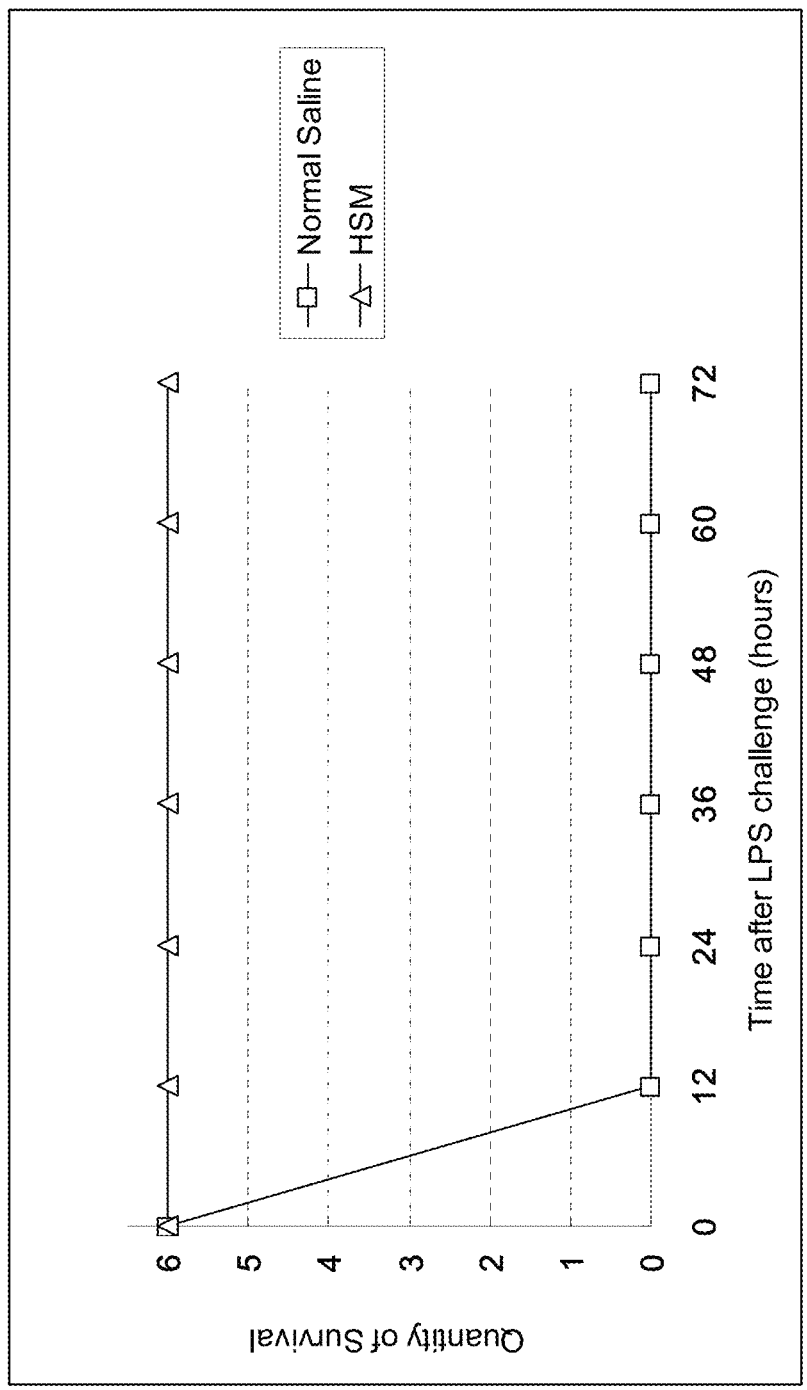
FIG. 20 shows the third re-examination of the efficacy of *Hirsutella sinensis* mycelia extract against LPS challenge.

Six-weeks-old BALB/c mice were pretreated with *Hirsutella sinensis* mycelia extract 48 hours before LPS challenge by i.p. of 120 mg of *Hirsutella sinensis* mycelia extract dissolved in normal saline. On day 0, 12 mice were challenged with LPS (0.25 mg/20 g mouse; 12.5 mg/Kg) intraperitoneally. The mortality of mice was monitored in 12 hr. intervals for 3 days. Data represent survival quantity (n=6). Study groups included normal saline pretreatment (Control) and *Hirsutella sinensis* mycelia pretreatment (HSM). The results are shown in FIG. 20. The results from FIG. 20 indicate *Hirsutella sinensis* mycelia can ameliorate the symptoms of the acute endotoxemia syndrome and significantly reduce LPS-induced sepsis mortality.

Example 12

Figure 21:
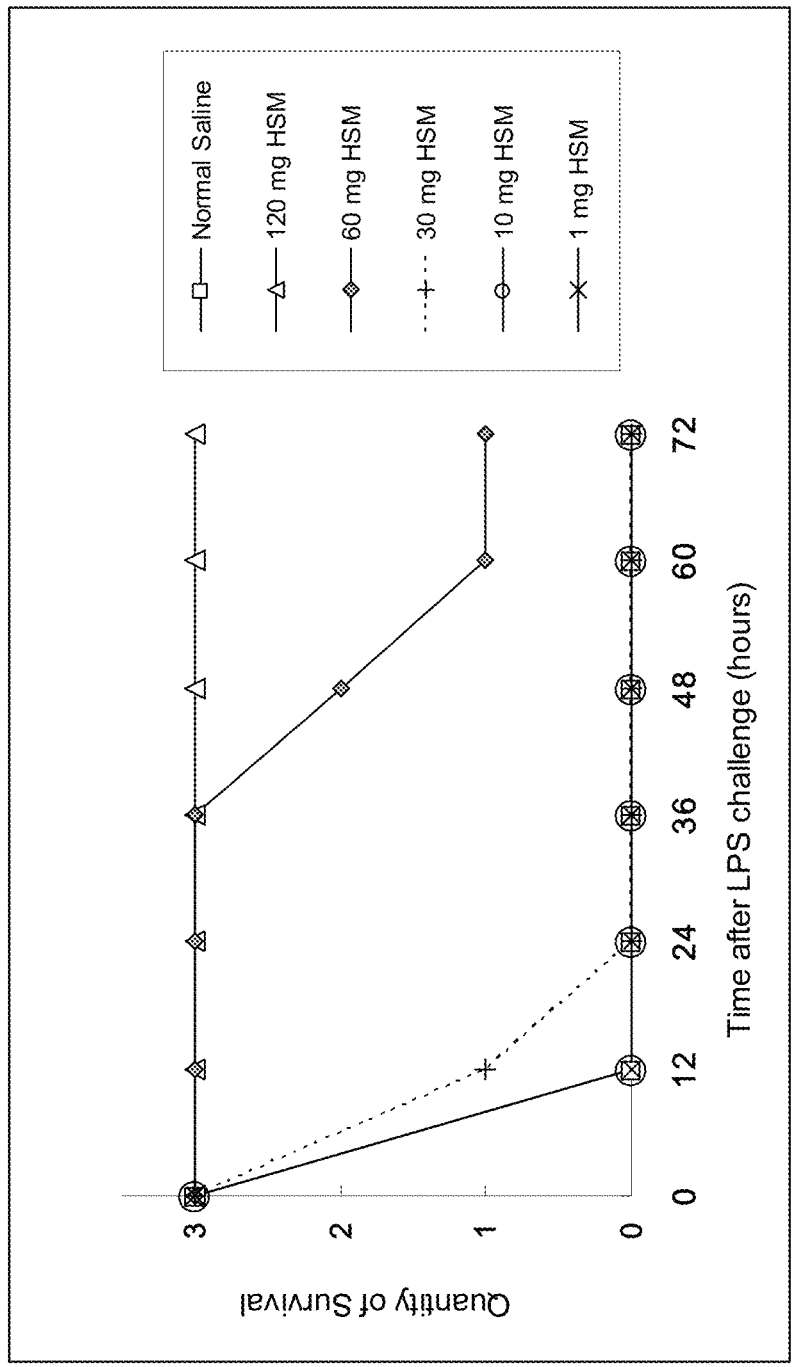
FIG. 21 demonstrates the dose effect of *Hirsutella sinensis* mycelia extract against LPS challenge.

Six-weeks-old BALB/c mice were pretreated with *Hirsutella sinensis* mycelia extract 48 hours before LPS challenge with i.p. of 1-120 mg of *Hirsutella sinensis* mycelia extract dissolved in normal saline. On day 0, 18 mice were challenged with LPS (025 mg/20 g mouse: 12.5 mg/Kg) intraperitoneally. The mortality of mice was monitored in 12-hour intervals for 3 days. Data represent survival quantity (n~3). Study groups included normal saline pretreatment (Control) and 1, 10, 30, 60, 120 mg *Hirsutella sinensis* mycelia pretreatment (HSM). The results are shown in FIG. 21. The results from FIG. 21 indicate the ability of *Hirsutella sinensis* mycelia to ameliorate the symptoms of acute endotoxemia syndrome and reduce LPS-induced sepsis mortality is in a dose-dependent manner.

Example 13

Figure 22:
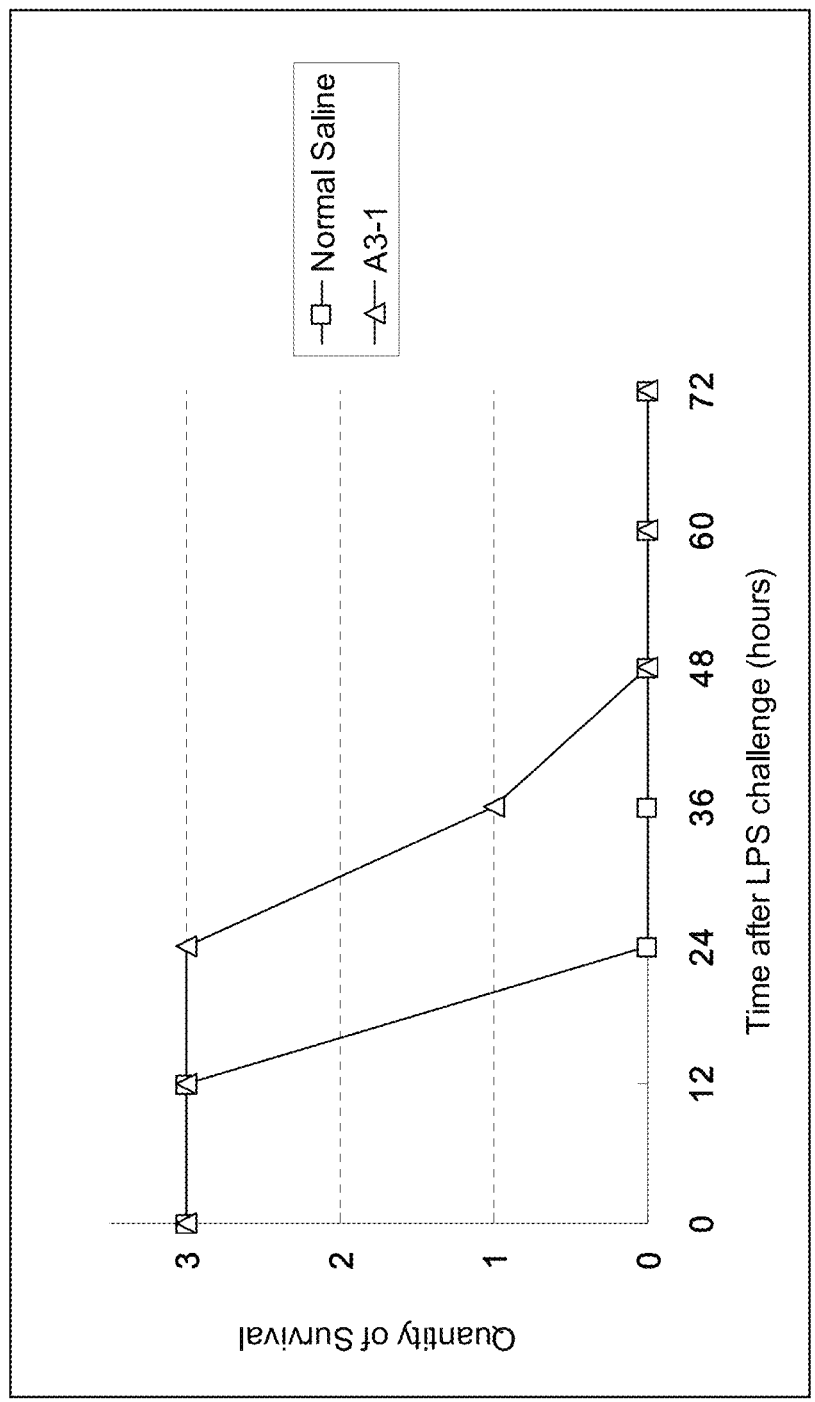
FIG. 22 demonstrates the efficacy of fraction A3-1 against LPS challenge.

Six-weeks-old BALB/c mice were pretreated with *Hirsutella sinensis* mycelia extract 48 hours before LPS challenge by intraperitoneal injection of 10 mg of fraction A3-1 dissolved in normal saline. On day 0, 6 mice were challenged with LPS (0.25 mg/20 g mouse; 12.5 mg/Kg) intraperitoneally. The mortality of mice was monitored in 12-hour intervals for 3 days., Data represent survival quantity (n=3). Study groups included normal saline pretreatment (Control) and A3-1 pretreatment (A34). The results are shown in FIG. 22. These results indicate that fraction A3-1 can ameliorate the symptoms of acute endotoxemia syndrome and significantly reduce LPS-induced sepsis mortality.

Example 14

Figure 23:
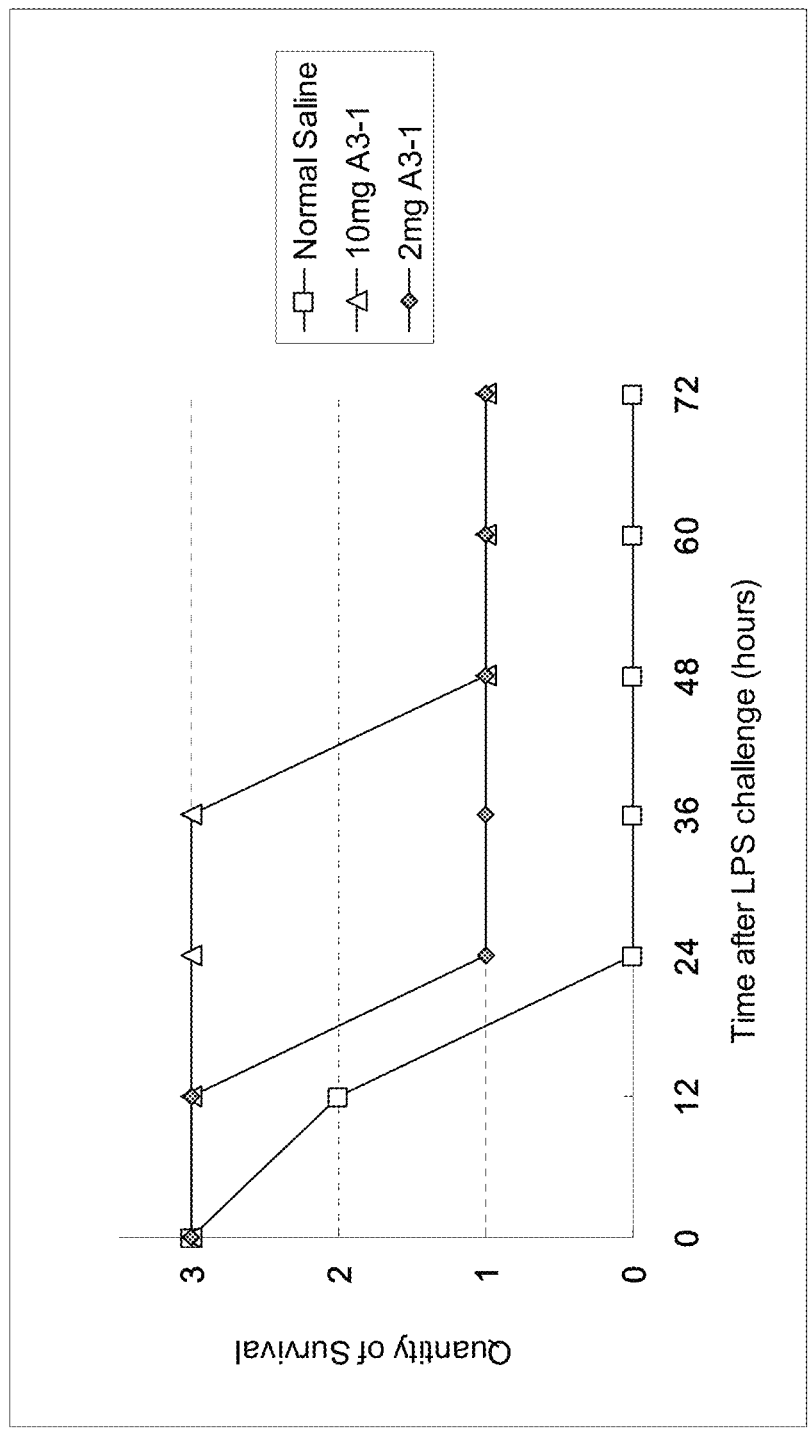
FIG. 23 shows the first re-examination of the effect of fraction A3-1 against LPS challenge.

Six-weeks-old BALB/c mice were pretreated with *Hirsutella sinensis* mycelia extract 48 hours before LPS challenge by i.p. of 2 or 10 mg of fraction A3-1 dissolved in normal saline. On day 0, 9 mice were challenged with LPS (0.25 mg/20 g mouse; 12.5 mg/Kg) intraperitoneally. The mortality of mice was monitored in 12-hours intervals for 3 days. Data represent survival quantity (n=3). Study groups included normal saline pretreatment (Control), 2 and 10 mg A3-1 pretreatment (A34). The results are shown in FIG. 23. The results from FIG. 23 indicate that fraction A3-1 can ameliorate the symptoms of the acute endotoxemia syndrome and significantly reduce LPS-induced sepsis mortality.

Example 15

Figure 24:
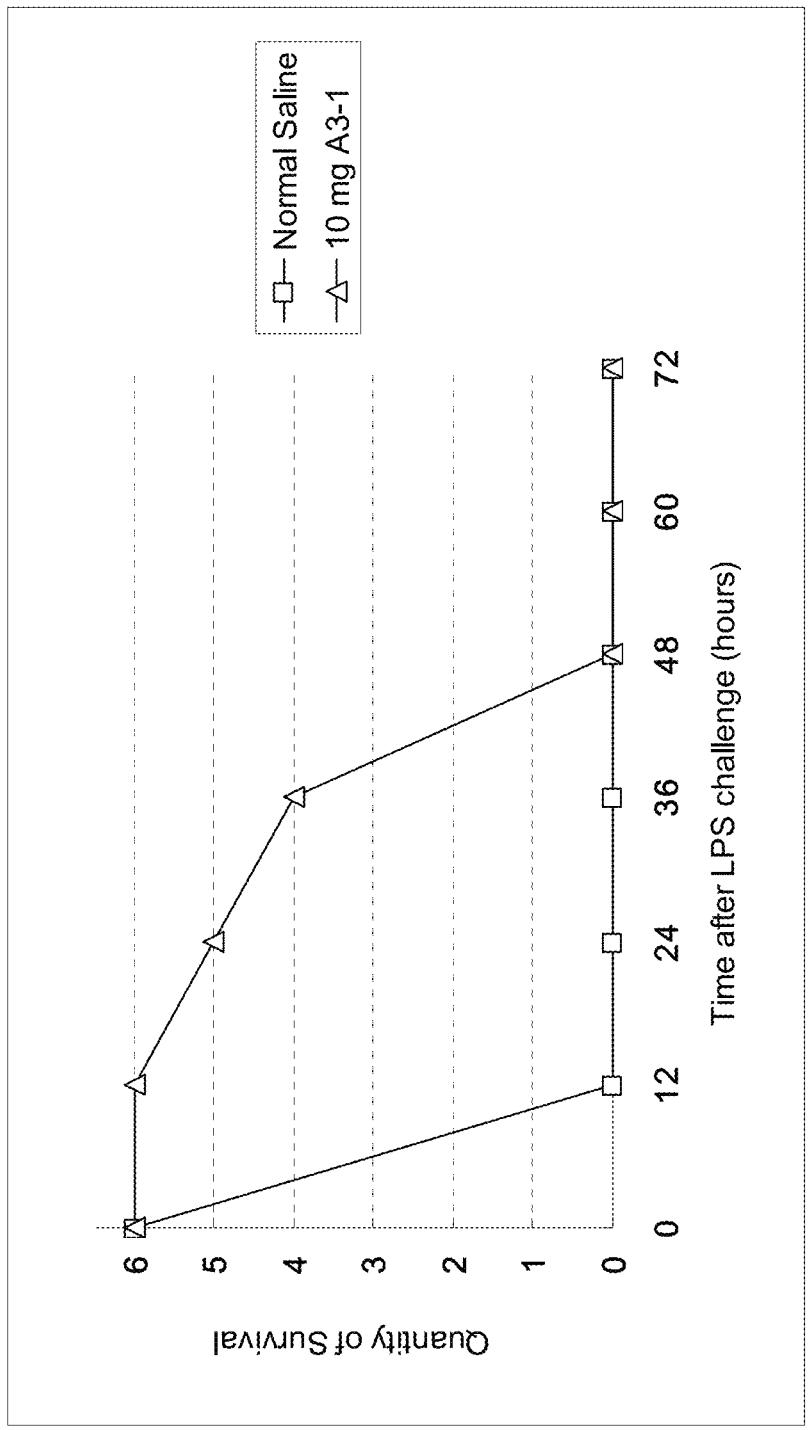
FIG. 24 shows the second re-examination of the effect of fraction A3-1 against LPS challenge.

Six-weeks-old BALB/c mice were pretreated with *Hirsutella sinensis* mycelia extract 48 hours before LPS challenge by i.p. of 10 mg of fraction A3-1 dissolved in normal saline. On day 0, 12 mice were challenged with LPS (0.25 mg/20 g mouse; 12.5 mg/Kg) intraperitoneally. The mortality of mice was monitored in 12 hour intervals for 3 days. Data represent survival quantity (n=6). Study groups included normal saline pretreatment (Control), 10 mg A3-1 pretreatment (A3-1). The results are shown in FIG. 24. The results from FIG. 24 indicate that fraction A3-1 can ameliorate the symptoms of the acute endotoxemia syndrome and significantly reduce LPS-induced sepsis mortality.

TABLE 5

Summary of efficacy of different doses of the *Hirsutella sinensis* mycelia extract and fractions A3-1 against LPS challenge.

| | Survival (%) | | | | | | | No. of test animals |
|---|---|---|---|---|---|---|---|---|
| | Hours after LPS | | | | | | | |
| Group | 0 | 12 | 24 | 36 | 48 | 60 | 72 | |
| Normal Saline | 100 | 56 | 0 | 0 | 0 | 0 | 0 | 18 |
| 120 mg HSM | 100 | 100 | 100 | 87 | 87 | 87 | 87 | 15 |
| 60 mg HSM | 100 | 100 | 100 | 100 | 67 | 33 | 33 | 3 |
| 30 mg HSM | 100 | 33 | 0 | 0 | 0 | 0 | 0 | 3 |
| 10 mg HSM | 100 | 0 | 0 | 0 | 0 | 0 | 0 | 3 |
| 1 mg HSM | 100 | 0 | 0 | 0 | 0 | 0 | 0 | 3 |
| 10 mg A3-1 | 100 | 100 | 89 | 78 | 11 | 11 | 11 | 9 |
| 4 mg A3-1 | 100 | 100 | 100 | 33 | 0 | 0 | 0 | 3 |
| 2 mg A3-1 | 100 | 100 | 33 | 33 | 33 | 33 | 33 | 3 |

Data represents survival percentage (%) following *Hirsutella sinensis* mycelia (HSM) pretreatment The results in Table 5 indicate higher HSM or A3-1 dosage may be beneficial to ameliorate the symptoms of the acute endotoxemia syndrome and increase LPS-induced sepsis survival rate.

Although specific embodiments of the invention have been described herein for purposes of illustration, various modifications may be made without deviating from the spirit and scope of the invention. Accordingly, the invention is not limited except as by the appended claims.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank® and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for treating an inflammatory response in a patient, the method comprising:
   administering a therapeutically effective amount of a formulation comprising an isolated partially purified sub-fraction of *Hirsutella sinensis* comprising at least 90% polysaccharides, wherein the partially purified polysaccharide sub-fraction is isolated from a water-soluble extract of *Hirsutella sinensis* mycelia, and wherein the polysaccharide sub-fraction is comprised of at least 50% galactose and at least 35% mannose and has a molecular weight of about 27.5 KDa,
   and optionally, comprising a pharmaceutically acceptable excipient, to a patient in need thereof,
   wherein the inflammatory response is due to sepsis or, acute endotoxemia syndrome, in a subject.

2. The method of claim 1, wherein the administering is by a method selected from intravenous, intradermal, subcutaneous, oral, inhalation, transdermal, topical, transmucosal, and rectal administration.

3. The method of claim 1, wherein the therapeutically effective amount is an amount sufficient to induce expression of IL-10, IL-1Ra and IL-1β.

4. The method of claim 1, wherein treating the inflammatory response comprises:
   increasing levels of one or more of the cytokines IFN-γ, IL-10, IL-6, or IL-1α in a mammalian cell.

5. The method of claim 1, wherein the treatment is therapeutic.

* * * * *